(12) United States Patent
Shimoma et al.

(10) Patent No.: US 11,434,238 B2
(45) Date of Patent: Sep. 6, 2022

(54) METHOD FOR PRODUCING TRIAZOLOPYRIDINE COMPOUND

(71) Applicant: JAPAN TOBACCO INC., Tokyo (JP)

(72) Inventors: Fumito Shimoma, Osaka (JP); Takashi Yamaguchi, Osaka (JP); Shoichi Sagawa, Osaka (JP)

(73) Assignee: Japan Tobacco Inc., Tokyo (JP)

( * ) Notice: Subject to any disclaimer, the term of this patent is extended or adjusted under 35 U.S.C. 154(b) by 0 days.

(21) Appl. No.: 16/463,216

(22) PCT Filed: Nov. 24, 2017

(86) PCT No.: PCT/JP2017/042239
§ 371 (c)(1),
(2) Date: Jun. 24, 2020

(87) PCT Pub. No.: WO2018/097254
PCT Pub. Date: May 31, 2018

(65) Prior Publication Data
US 2020/0339563 A1    Oct. 29, 2020

(30) Foreign Application Priority Data

Nov. 25, 2016  (JP) .............................. JP2016-228897

(51) Int. Cl.
*C07D 471/04*    (2006.01)
(52) U.S. Cl.
CPC .................. *C07D 471/04* (2013.01)
(58) Field of Classification Search
CPC .................................................. C07D 471/04
See application file for complete search history.

(56) References Cited

U.S. PATENT DOCUMENTS

2011/0077267 A1* 3/2011 Mitani ...................... A61P 7/06
546/120

FOREIGN PATENT DOCUMENTS

| JP | WO2011007856 | 1/2011 |
| JP | WO2016190420 | 12/2016 |
| WO | WO2017083431 | 5/2017 |

OTHER PUBLICATIONS

Dorwald et al., Side reactions in Organic Synthesis, Wiley: VCH Weinheim Preface, pp. 1-15 and Chapter 8, pp. 279-308. (Year: 2005).*
Colbon et al., "A general and efficient route to 6-methyl-pyrazin-2-yl-amines: alkylation of 2, 6-dichloropyrazine vie malonate derivatives", Journal of Heterocyclic Chemistry, 2008, 45(5):1451-1456.
Donald et al., "An efficient synthesis of 2-alkylpyridines using an slkylation/double decarboxylation strategy", Tetrahedron Letters, 2012, 53(30:3853-3856.
PCT International Search Report and Written Opinion in International Application No. PCT/JP2017/042239, dated Jan. 9, 2018, 16 pages with english translation.

* cited by examiner

*Primary Examiner* — John S Kenyon
(74) *Attorney, Agent, or Firm* — Fish & Richardson P.C.

(57) ABSTRACT

The present invention relates to a novel method for producing a triazolopyridine compound or a salt thereof having a PHD inhibitory action and useful for treating or preventing diseases caused by decreased production of EPO, or the like. The present invention provides a method for producing 2-({[7-hydroxy-5-(2-phenylethyl)-[1,2,4]triazolo[1,5-a]pyridin-8-yl]carbonyl}amino)acetic acid comprising a step of reacting Compound [VI]:

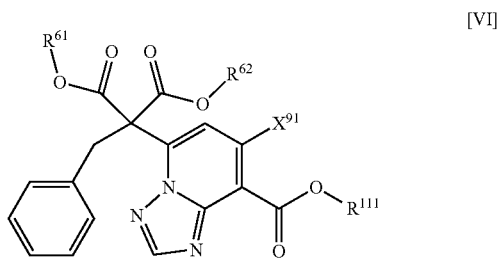

wherein $R^{61}$, $R^{62}$ and $R^{111}$ are as defined in the specification, or a salt thereof.

9 Claims, 6 Drawing Sheets

METHOD FOR PRODUCING TRIAZOLOPYRIDINE COMPOUND

TECHNICAL FIELD

The present invention relates to a novel method for producing a triazolopyridine compound or a salt thereof useful as an inhibitor of prolyl hydroxygenase (PHD), and an intermediate thereof.

BACKGROUND ART

Patent Document 1 describes a compound useful as a PHD inhibitor and a production method thereof.

DOCUMENT LIST

Patent Document

Patent Document 1: WO 2011/007856

SUMMARY OF THE INVENTION

The present invention aims to provide a novel method for producing a triazolopyridine compound or a salt thereof useful for treating or preventing diseases caused by decreased production of erythropoietin (EPO) and the like.

One embodiment of the present invention is as shown in the following [1] to [10].

[1] A method for producing 2-({[7-hydroxy-5-(2-phenylethyl)-[1,2,4]triazolo[1,5-a]pyridin-8-yl]carbonyl}amino)acetic acid (Compound (1):

(1)

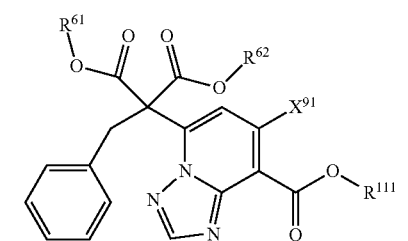

or a pharmaceutically acceptable salt thereof, the method comprising:

a step of hydrolyzing and then decarboxylating Compound [VI]:

[VI]

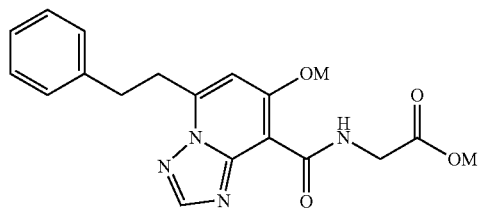

wherein $R^{61}$, $R^{62}$ and $R^{111}$ are each independently a carboxy-protecting group and $X^{91}$ is a leaving group, or a salt thereof to give Compound [IV]:

[IV]

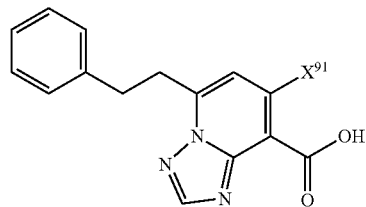

wherein $X^{91}$ is as defined above, or a salt thereof, a step of reacting Compound [IV] or a salt thereof with a glycine derivative to give Compound [III]:

[III]

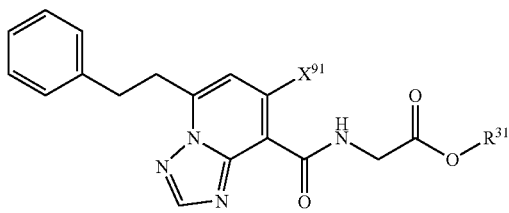

wherein $R''$ is a carboxy-protecting group and $X^{91}$ is as defined above, or a salt thereof, a step of reacting Compound [III] or a salt thereof with a base to give Compound [II]:

[II]

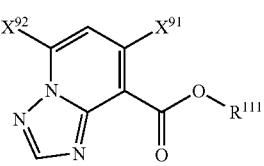

wherein each M is the same and is a metal species which forms a salt with both a hydroxy group and a carboxy group (a salt of Compound (1)), and a step of reacting Compound [II] (the said salt of Compound (1)) with an acid to give Compound (1).

[2] The production method of [1] further comprising:

a step of reacting Compound [VII]:

[VII]

wherein $X^{92}$ is a leaving group and $X^{91}$ and $R^{111}$ are as defined above, or a salt thereof with a benzylmalonic acid derivative to give Compound [VI] or a salt thereof.

[3] The production method of [2] further comprising:
a step of reacting Compound [XI]:

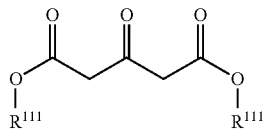

wherein $R^{111}$ is as defined above and may be the same or different, with cyanamide or a salt thereof to give Compound [X]:

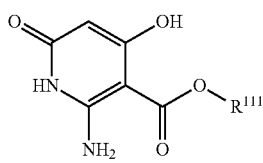

wherein $R^{111}$ is as defined above, or a salt thereof,
a step of converting a hydroxy group of Compound [X] or a salt thereof to a leaving group to give Compound [IX]:

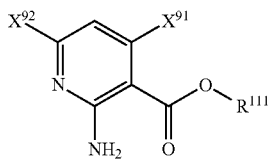

wherein $X^{91}$, $X^{92}$ and $R^{111}$ are as defined above, or a salt thereof,
a step of sequentially reacting Compound [IX] or a salt thereof with N,N-dimethylformamide dialkylacetal, hydroxylamine or a salt thereof to give Compound [VIII]:

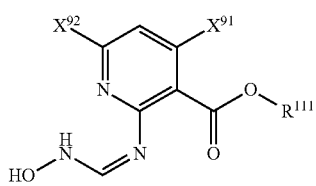

wherein $X^{91}$, $X^{92}$ and $R^{111}$ are as defined above, or a salt thereof, and
a step of subjecting Compound [VIII] or a salt thereof to a dehydration reaction to give Compound [VII] or a salt thereof.

[4] The production method of [1] wherein Compound [VI] or a salt thereof is Compound (6):

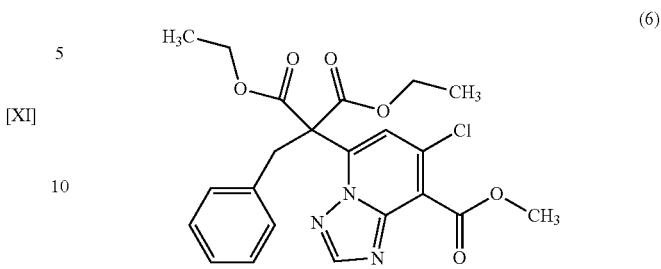

or a salt thereof, Compound [IV] or a salt thereof is Compound (4):

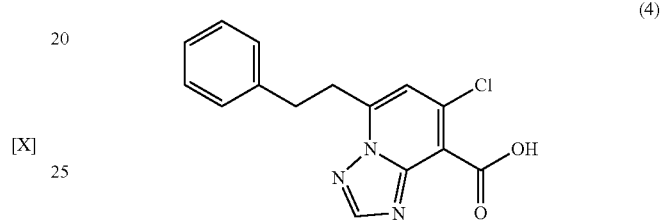

or a salt thereof, Compound [III] or a salt thereof is Compound (3):

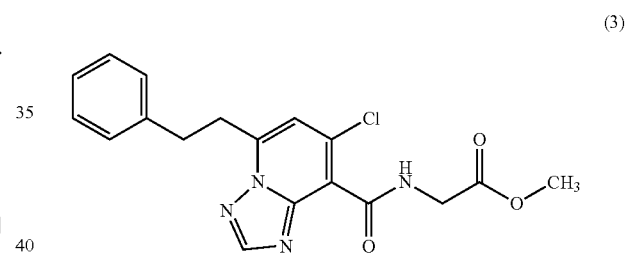

or a salt thereof, and Compound [II] (the said salt of Compound (1)) is Compound (2):

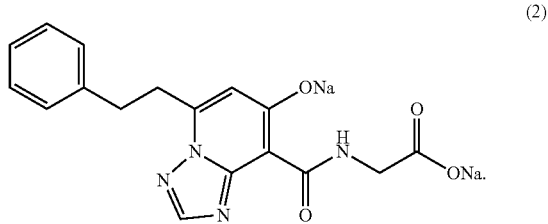

[5] The production method of [4] further comprising:
a step of reacting Compound (7):

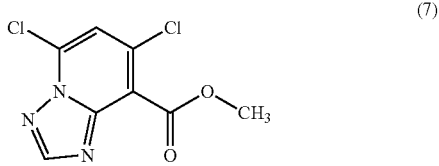

or a salt thereof with a benzylmalonic acid derivative to give Compound (6) or a salt thereof.

[6] The production method of [5] further comprising:
a step of reacting Compound (11):

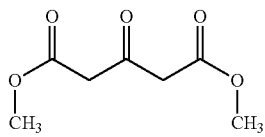
(11)

with cyanamide or a salt thereof to give Compound (10):

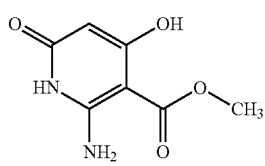
(10)

or a salt thereof, a step of chlorinating a hydroxy group of Compound (10) or a salt thereof to give Compound (9):

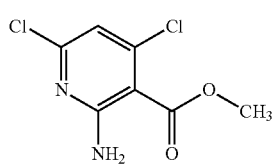
(9)

or a salt thereof,
a step of reacting Compound (9) or a salt thereof with hydroxylamine or a salt thereof to give Compound (8):

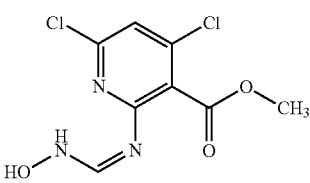
(8)

or a salt thereof, and
a step of subjecting Compound (8) or a salt thereof to a dehydration reaction to give Compound (7) or a salt thereof.

[7] A method for producing Compound [VI]:

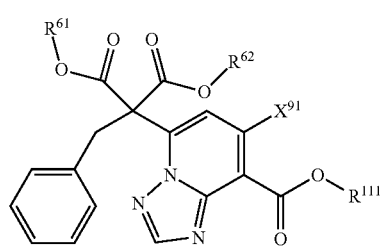
[VI]

wherein $R^{61}$ and $R^{62}$ are each independently a carboxy-protecting group, $X^{91}$ is a leaving group and $R^{111}$ is a carboxy-protecting group, or a salt thereof, the method comprising:
a step of reacting Compound [VII]:

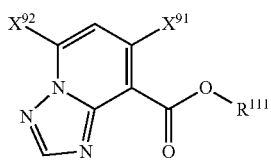
[VII]

wherein $X^{92}$ is a leaving group and $X^{91}$ and $R^{111}$ are as defined above, or a salt thereof with a benzylmalonic acid derivative to give Compound [VI] or a salt thereof.

[8] A method for producing Compound [IV]:

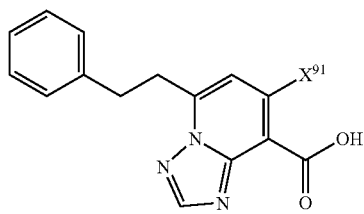
[IV]

wherein $X^{51}$ is a leaving group, or a salt thereof, the method comprising:
a step of reacting Compound [VII]:

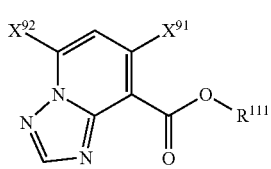
[VII]

wherein $X^{92}$ is a leaving group, $R^{111}$ is a carboxy-protecting group and $X^{91}$ is as defined above, or a salt thereof with a benzylmalonic acid derivative to give Compound [VI]:

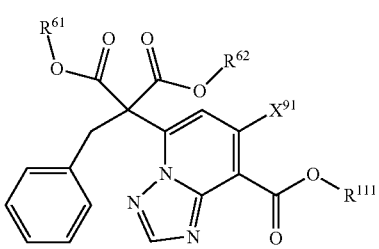
[VI]

wherein $R^{61}$ and $R^{62}$ are each independently a carboxy-protecting group and $X^{91}$ and $R^{111}$ are as defined above, or a salt thereof, and
a step of hydrolyzing and then decarboxylating Compound [VI] or a salt thereof to give Compound [IV] or a salt thereof.

[9] Compound [VI]:

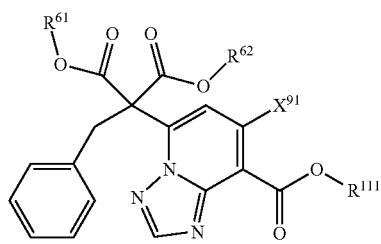

[VI]

wherein $R^{61}$, $R^{62}$ and $R^{111}$ are each independently a carboxy-protecting group and $X^{91}$ is a leaving group, or a salt thereof.

[10] Compound [V-1]:

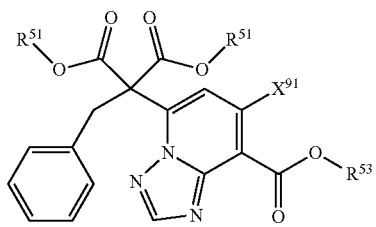

[V-1]

wherein $R^{51}$ and $R^{53}$ are each independently a hydrogen atom or a metal species which forms a salt with a carboxy group, $R^{51}$ may be the same or different and $X^{91}$ is a leaving group.

Effect of the Invention

According to the production method of the present invention, a triazolopyridine compound having a PHD inhibitory action and useful for treating or preventing diseases caused by decreased production of EPO can be produced in a high yield by a simple operation via a compound which is easy to handle. The method can also provide a novel intermediate for synthesizing the triazolopyridine compound.

DESCRIPTION OF EMBODIMENTS

Figure 1:
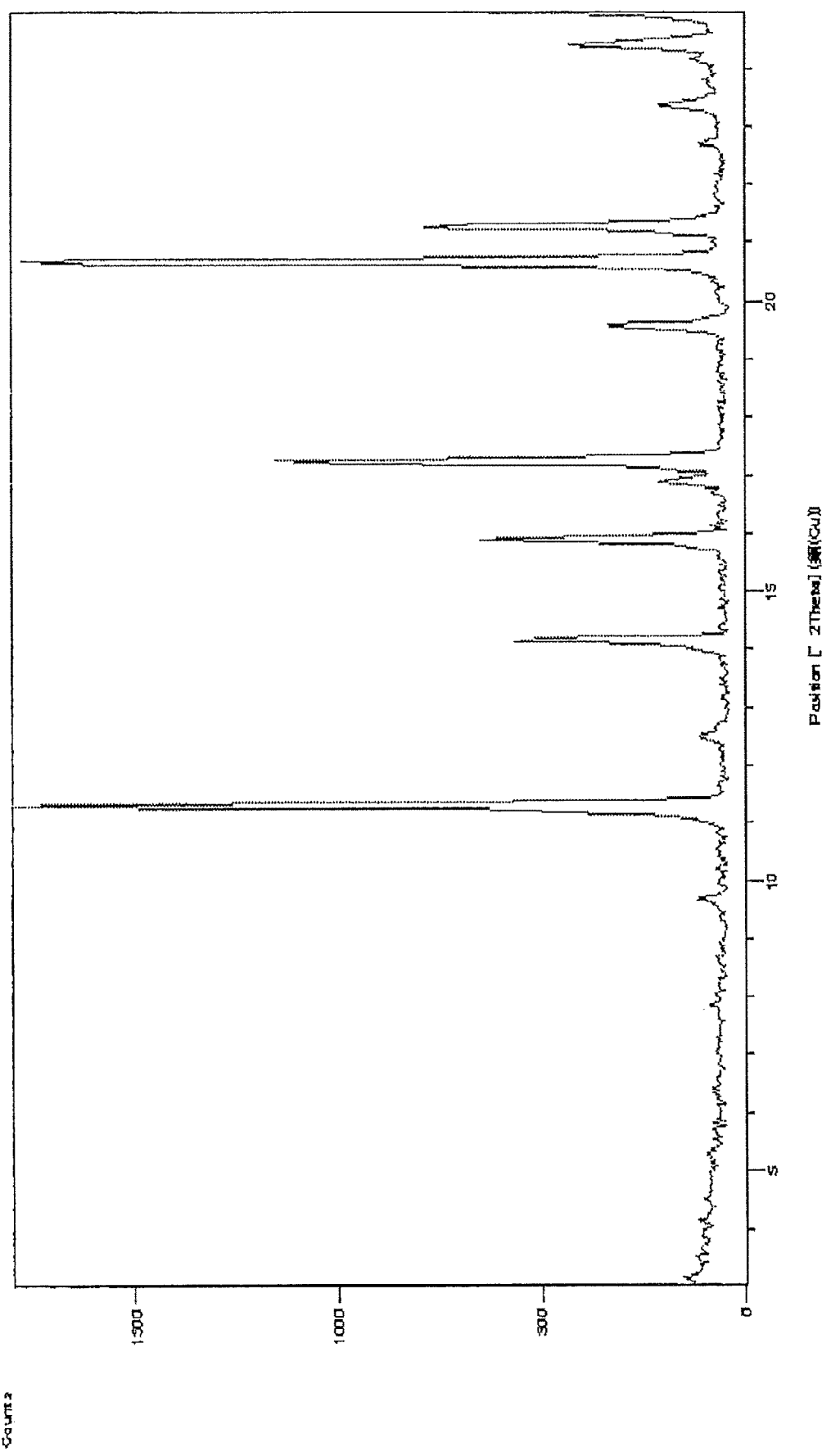
FIG. 1 shows a powder X-ray diffraction pattern of a crystal of Compound (7) synthesized in Step 4 of Example 1.

The definitions of the terms in the present specification are as follows.

The "halogen" is, for example, fluorine, chlorine, bromine, iodine or the like. Chlorine or bromine is preferable and chlorine is particularly preferable.

The "$C_{1-6}$ alkyl" is a straight or branched chain alkyl having 1 to 6 carbon atoms, preferably a straight or branched chain alkyl having 1 to 4 carbon atoms. Examples include methyl, ethyl, propyl, isopropyl, butyl, isobutyl, sec-butyl, tert-butyl, pentyl, isopentyl, tert-pentyl, 1-ethylpropyl, neopentyl, hexyl, 2-ethylbutyl, 3,3-dimethylbutyl and the like. Methyl, ethyl, propyl, isopropyl, butyl, isobutyl, sec-butyl or tert-butyl is preferable and methyl or ethyl is particularly preferable.

The "leaving group" refers to a leaving group generally used in the technical field of organic chemistry and includes, for example, halogen, p-toluenesulfonyloxy, methanesulfonyloxy, trifluoromethanesulfonyloxy, trifluoroacetyloxy and the like.

As for the leaving group for $X^{91}$ in compounds [III], [IV], [V-1], [V-2], [V-3], [V-4], [VI], [VII], [VIII] and [IX] or the leaving group for $X^{92}$ in compounds [VII], [VIII] and [IX], halogen is preferable, and chlorine is particularly preferable.

The "same metal species which forms a salt with both a hydroxy group and a carboxy group" may be any metal atom as long as it can form a salt with both a hydroxy group (particularly, hydroxy group bonded to aromatic ring) and a carboxy group by a neutralization reaction and includes, for example, lithium, sodium, potassium, calcium, magnesium and the like.

As for the same metal species which forms a salt with both a hydroxy group and a carboxy group for M in Compound [II], sodium is preferable.

The "metal species which forms a salt with a carboxy group" may be any metal atom as long as it can form a salt with a carboxy group by a neutralization reaction and includes, for example, lithium, sodium, potassium, calcium, magnesium and the like.

As for the metal species which forms a salt with a carboxy group for $R^{51}$ or $R^{53}$ in compounds [V-1] and [V-2], sodium is preferable.

The "carboxy-protecting group" is a substituent generally used in the technical field of organic chemistry to substitute a hydrogen atom for protecting a carboxy group from its high reactivity. Representative examples of the "carboxy-protecting group" include groups described in Wiley-Interscience 2007 "Protective Groups in Organic Synthesis, 4th Ed." (Theodora W. Greene, Peter G. M. Wuts); Thieme 2004 "Protecting Groups 3rd Ed." (P. J. Kocienski) and the like. The "carboxy-protecting group" includes, for example, $C_{1-6}$ alkyl, benzyl and the like.

As for the carboxy-protecting group for $R^{31}$ in Compound [III], methyl is preferable.

As for the carboxy-protecting group for $R^{61}$ or $R^{62}$ in Compound [VI], ethyl is preferable.

As for the carboxy-protecting group for $R^{111}$ in compounds [VI], [VII], [VIII], [IX], [X] and [XI], methyl is preferable.

The "glycine derivative" is Glycine Derivative [XIII]:

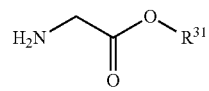

[XIII]

wherein $R^{31}$ is a carboxy-protecting group, or a salt thereof.

As for the carboxy-protecting group for $R^{31}$ in Glycine Derivative [XIII], methyl is preferable, which is the same as in Compound [III].

The "benzylmalonic acid derivative" is Benzylmalonic Acid Derivative [XVI]:

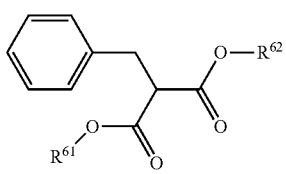

[XVI]

wherein $R^{61}$ and $R^{62}$ are each independently a carboxy-protecting group.

As for the carboxy-protecting group for $R^{61}$ or $R^{62}$ in Benzylmalonic Acid Derivative [XVI], ethyl is preferable, which is the same as in Compound [VI].

The "pharmaceutically acceptable salt" of the compound may be any salt as long as it forms a nontoxic salt with the compound of the present invention and includes, for example, salts with inorganic acids, salts with organic acids, salts with inorganic bases, salts with organic bases, salts with amino acids and the like.

Examples of the salt with inorganic acid include salts with hydrochloric acid, nitric acid, sulfuric acid, phosphoric acid, hydrobromic acid and the like.

Examples of the salt with organic acid include salts with oxalic acid, maleic acid, citric acid, fumaric acid, lactic acid, malic acid, succinic acid, tartaric acid, acetic acid, trifluoroacetic acid, gluconic acid, ascorbic acid, methanesulfonic acid, benzenesulfonic acid, p-toluenesulfonic acid and the like.

Examples of the salt with inorganic base include sodium salt, potassium salt, calcium salt, magnesium salt, ammonium salt and the like.

Examples of the salt with organic base include salts with methylamine, diethylamine, trimethylamine, triethylamine, ethanolamine, diethanolamine, triethanolamine, ethylenediamine, tris(hydroxymethyl)methylamine, dicyclohexylamine, N,N'-dibenzylethylenediamine, guanidine, pyridine, picoline, choline, cinchonine, meglumine and the like.

Examples of the salt with amino acid include salts with lysine, arginine, aspartic acid, glutamic acid and the like.

The "salt" of the compound may be any salt as long as it forms a salt with the compound of the present invention and includes, for example, salts with inorganic acids, salts with organic acids, salts with inorganic bases, salts with organic bases, salts with amino acids and the like.

Examples of the salt with inorganic acid include salts with hydrochloric acid, nitric acid, sulfuric acid, phosphoric acid, hydrobromic acid and the like.

Examples of the salt with organic acid include salts with oxalic acid, maleic acid, citric acid, fumaric acid, lactic acid, malic acid, succinic acid, tartaric acid, acetic acid, trifluoroacetic acid, gluconic acid, ascorbic acid, methanesulfonic acid, benzenesulfonic acid, p-toluenesulfonic acid and the like.

Examples of the salt with inorganic base include sodium salt, potassium salt, calcium salt, magnesium salt, ammonium salt and the like.

Examples of the salt with organic base include salts with methylamine, diethylamine, trimethylamine, triethylamine, ethanolamine, diethanolamine, triethanolamine, ethylenediamine, tris(hydroxymethyl)methylamine, dicyclohexylamine, N,N'-dibenzylethylenediamine, guanidine, pyridine, picoline, choline, cinchonine, meglumine and the like.

Examples of the salt with amino acid include salts with lysine, arginine, aspartic acid, glutamic acid and the like.

As for the salt of Compound [IV], sodium salt or hydrochloride is preferable.

As for the salt of Compound [VII], hydrochloride is preferable.

As for a salt of hydroxylamine to be reacted with Compound [IX] or a salt thereof to obtain Compound [VIII] or a salt thereof, hydrochloride is preferable.

As for the salt of Glycine Derivative [XIII], hydrochloride is preferable.

The compound, a salt thereof or a pharmaceutically acceptable salt thereof disclosed in the present specification may exist as a solvate. The "solvate" refers to a compound, a salt thereof or a pharmaceutically acceptable salt thereof disclosed in the present specification with which a solvent molecule is coordinated, and also includes hydrates. The solvate is preferably a pharmaceutically acceptable solvate and includes, for example, hydrate, ethanol solvate, dimethyl sulfoxide-solvate and the like of the compound, a salt thereof or a pharmaceutically acceptable salt thereof disclosed in the present specification. Specific examples include hemihydrate, monohydrate, dihydrate or mono(ethanol)solvate of the compound disclosed in the present specification or a monohydrate of a disodium salt of the compound described in the present specification and the like.

The solvates can be produced according to conventional methods.

As for a salt of Compound (1) with a base (Compound [II]) to be reacted with an acid to obtain Compound [I], Compound (2):

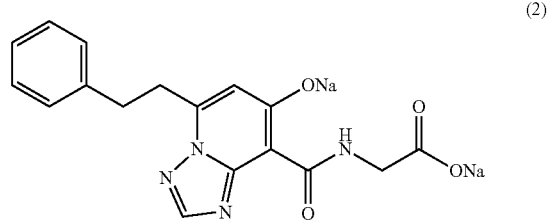

(2)

is preferable. Alternatively, Compound (2) may also be a solvate thereof. As for the solvate of Compound (2), a hydrate of Compound (2) is preferable and a monohydrate of Compound (2) is particularly preferable.

As for Compound [III] or a salt thereof with an acid, Compound (3):

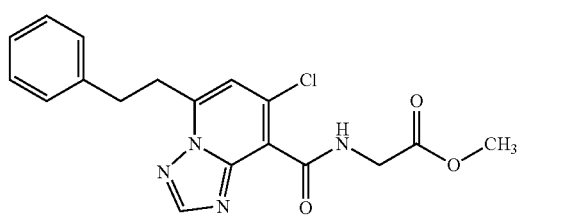

(3)

or a salt thereof with an acid is preferable and Compound (3) is particularly preferable.

As for Compound [IV] or a salt thereof with an acid or base, Compound (4):

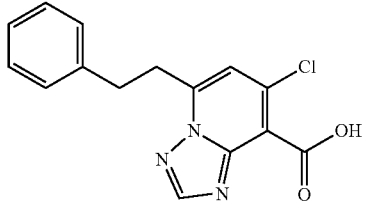

(4)

or a salt thereof with an acid or base is preferable and Compound (4) is particularly preferable.

As for Compound [V-1], Compound (5-1):

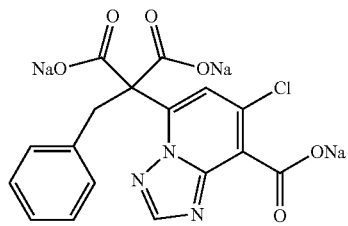

(5-1)

is preferable.

As for Compound [V-2], Compound (5-2):

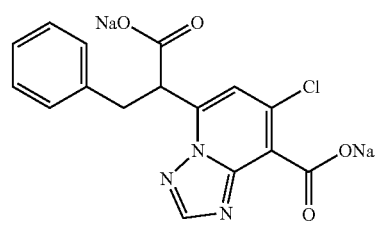

(5-2)

is preferable.

As for Compound [V-3], Compound (5-3):

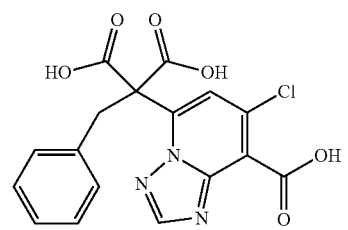

(5-3)

is preferable.

As for Compound [V-4], Compound (5-4):

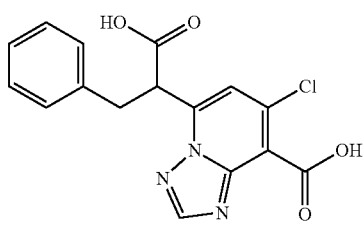

(5-4)

is preferable.

As for Compound [VI] or a salt thereof with an acid, Compound (6):

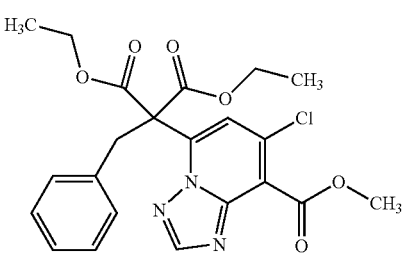

(6)

or a salt thereof with an acid is preferable and Compound (6) is particularly preferable.

As for Compound [VII] or a salt thereof with an acid, Compound (7):

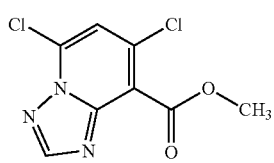

(7)

or a salt thereof with an acid is preferable and Compound (7) is particularly preferable.

As for Compound [VIII] or a salt thereof with an acid, Compound (8):

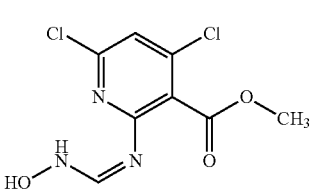

(8)

or a salt thereof with an acid is preferable and Compound (8) is particularly preferable.

As for Compound [IX] or a salt thereof with an acid, Compound (9):

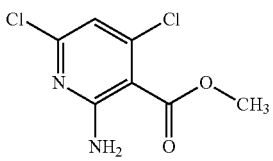

or a salt thereof with an acid is preferable and Compound (9) is particularly preferable.

As for Compound [X] or a salt thereof with an acid, Compound (10):

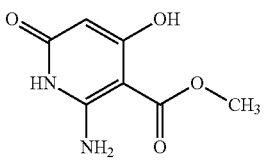

or a salt thereof with an acid is preferable and Compound (10) is particularly preferable.

As for Compound [XI], Compound (11):

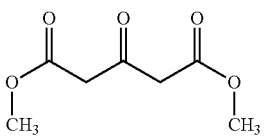

is preferable.

As for Glycine Derivative [XIII] or a salt thereof, methyl glycinate (Compound (13):

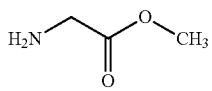

or a salt thereof is preferable and methyl glycinate hydrochloride is particularly preferable.

As for Benzylmalonic Acid Derivative [XVI], diethyl benzylmalonate (Compound (16):

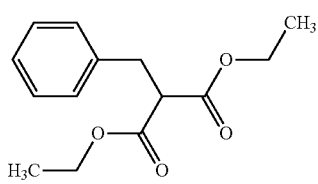

is preferable.

The compound disclosed in the present specification may exist as a tautomer; and in this case, the compound of the present invention may exist as each tautomer or a mixture of a tautomer.

The compound disclosed in the present specification may have one or more asymmetric carbons; and in this case, the compound disclosed in the present specification may exist as a single enantiomer, a single diastereomer, a mixture of an enantiomer or a mixture of a diastereomer.

The compound disclosed in the present specification may simultaneously contain plural structural characteristics that produce the above-mentioned isomers. The compound disclosed in the present specification may contain the above-mentioned isomers at any ratio.

In the absence of other reference such as annotation and the like, the formulas, chemical structures and compound names indicated in the present specification without specifying the stereochemistry thereof encompass all the above-mentioned isomers that may exist.

A diastereomeric mixture can be separated into each diastereomer by conventional methods such as chromatography, crystallization and the like. In addition, each diastereomer can also be prepared by using a stereochemically single starting material, or by a synthetic method using a stereoselective reaction.

An enantiomeric mixture can be separated into each single enantiomer by a method well known in the art.

For example, an enantiomeric mixture may be reacted with a substantially pure enantiomer which is known as a chiral auxiliary to form a diastereomeric mixture, which may be then isolated into a diastereomer with an enhanced isomeric ratio or a substantially pure single diastereomer by a standard method such as fractionated crystallization or chromatography. The added chiral auxiliary may be removed from the isolated diastereomer by a cleavage reaction to give a desirable enantiomer.

In addition, an enantiomeric mixture of a compound can also be directly separated by a chromatography method using a chiral solid phase well known in the art.

Alternatively, one of the enantiomers of the compound can also be obtained by using a substantially pure optically active starting material or by stereoselective synthesis (asymmetric induction) using a prochiral intermediate and a chiral auxiliary or an asymmetric catalyst.

The absolute steric configuration can be determined based on the X-ray crystal analysis of the resultant crystalline product or intermediate; and in this case, a resultant crystalline product or intermediate derivatized with a reagent having an asymmetric center with a known steric configuration may be used where necessary.

The X-ray crystal analysis method includes crystal analysis by a powder X-ray diffraction method.

The peak of the spectrum obtained by the above-mentioned analysis method inevitably contains certain measurement errors due to the instruments used for measurement, sample preparation, data analysis methods, and the like.

Therefore, the X-ray diffraction measurement values of crystals disclosed in the present specification contain an error ±0.2° of the obtained diffraction angle 2 θ.

The production method of the present invention is specifically described in the following.

In each step, a reaction workup may be performed according to a method generally employed. The resultant product may be purified by appropriately selecting a conventional method such as distillation, crystallization, recrystallization, column chromatography, preparative HPLC, slurry wash and the like, or using them in combination. It is also possible to proceed to a next step without performing isolation or purification. Each step may be performed under inert gas, for example, under nitrogen flow.

Step 1

Part 1

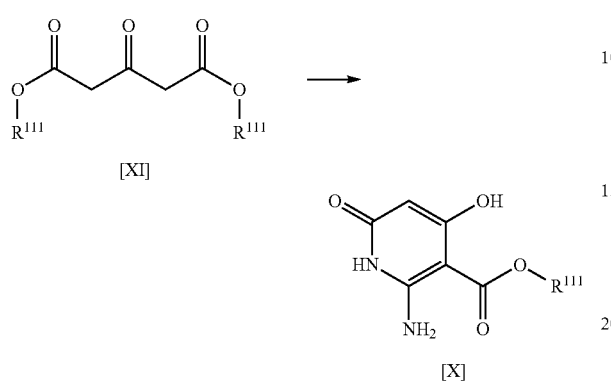

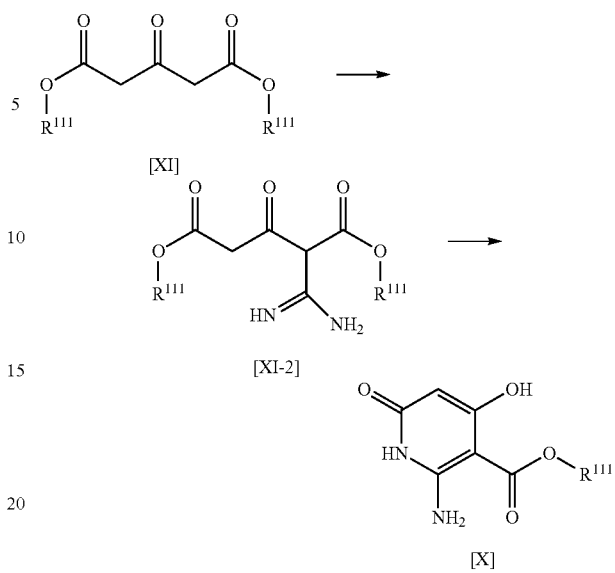

wherein $R^{111}$ is a carboxy-protecting group, and $R^{111}$ in Compound [XI] may be the same or different.

Compound [X] or a salt thereof with an acid or base (preferably, Compound [X]) is obtained by reacting Compound [XI] with cyanamide or a salt thereof (preferably, cyanamide). For example, the reaction can be performed by the method described in Prezent, M. A. & Dorokhov, V. A. Russian Chemical Bulletin (2005) Vol. 54: pp. 1343-1345.

The reaction is performed in a solvent in the presence of a metal catalyst such as nickel (II) acetylacetonate and the like.

Examples of the solvent include hexane, ethyl acetate, chloroform, methylene chloride, toluene, 1,4-dioxane, tetrahydrofuran, 1,2-dimethoxyethane, methanol, ethanol, 2-propanol, dimethyl sulfoxide, N,N-dimethylformamide, N-methyl-2-pyrrolidone, acetonitrile, water, or a mixture thereof. Among the examples, 1,2-dimethoxyethane is preferable.

Cyanamide or a salt thereof is used in 1 equivalent to 10 equivalents, preferably 3 equivalents to 5 equivalents, particularly preferably 3 equivalents, relative to Compound [XI].

The metal catalyst is used in 0.05 equivalents to 1 equivalent, preferably 0.1 equivalent to 0.3 equivalents, particularly preferably 0.1 equivalent, relative to Compound [XI].

The reaction temperature and reaction time are 0° C. to the boiling point of the solvent for 0.5 hr to 72 hr, preferably 0° C. to the boiling point of the solvent for 1 hr to 20 hr. Since the reaction is exothermic, it is preferable to perform stepwise heating to prevent a rapid temperature rise.

Part 2

As shown in the following formulas, Compound [XI] is reacted with cyanamide or a salt thereof (preferably, cyanamide) and production of a reaction intermediate, Compound [XI-2] is confirmed by high performance liquid chromatography, after which Compound [X] or a salt thereof with an acid or base (preferably, Compound [X]) is obtained by a method including reacting Compound [XI-2] with a base.

Compared with the method of the said Part 1, the method of Part 2 can reduce the amount of cyanamide or a salt thereof to be used relative to Compound [XI] and can increase the amount of Compound [X] obtained relative to Compound [XI].

The reaction to produce Compound [XI-2] is performed using Compound [XI] and cyanamide or a salt thereof (preferably, cyanamide) in a solvent in the presence of a metal catalyst such as nickel (II) acetate, nickel (II) chloride, nickel (II) acetylacetonate and the like.

Examples of the solvent include hexane, ethyl acetate, chloroform, methylene chloride, toluene, 1,4-dioxane, tetrahydrofuran, 1,2-dimethoxyethane, methanol, ethanol, 2-propanol, dimethyl sulfoxide, N,N-dimethylformamide, N-methyl-2-pyrrolidone, acetonitrile, water, or a mixture thereof. Among the examples, acetonitrile is preferable.

Cyanamide or a salt thereof is added in 1 equivalent to equivalents, preferably 1 equivalent to 1.5 equivalents, particularly preferably 1.05 equivalents, relative to Compound [XI].

The metal catalyst is used in 0.05 equivalents to 1 equivalent, preferably 0.05 equivalents to 0.1 equivalent, relative to Compound [XI].

An acid such as acetic acid and the like may be added as an additive. The amount is 0 equivalent to 0.2 equivalents, preferably 0.1 equivalent, relative to Compound [XI].

The reaction temperature and reaction time are 0° C. to the boiling point of the solvent for 24 hr to 300 hr. The reaction temperature is preferably 20° C. to 35° C.

The reaction to produce Compound [X] from Compound [XI-2] is performed using Compound [XI-2] in a solvent in the presence of a base such as sodium hydroxide, potassium hydroxide, lithium hydroxide, sodium acetate, potassium acetate, ammonia and the like.

Examples of the solvent include chloroform, methylene chloride, toluene, 1,4-dioxane, tetrahydrofuran, 1,2-dimethoxyethane, methanol, ethanol, 2-propanol, dimethyl sulfoxide, N,N-dimethylformamide, N-methyl-2-pyrrolidone, acetonitrile, water, or a mixture thereof. Among the examples, acetonitrile is preferable.

The base is used in 1 equivalent to 2.0 equivalents, preferably 1 equivalent, relative to Compound [XI].

The reaction temperature and reaction time are 0° C. to 50° C. for 0.1 hr to 12 hr, preferably 25° C. for 0.1 hr to 1 hr.

After completion of the reaction in this step and before performing the reaction of the next step, Compound [X] or a salt thereof with an acid or base is preferably isolated to mainly remove impurities.

Step 2

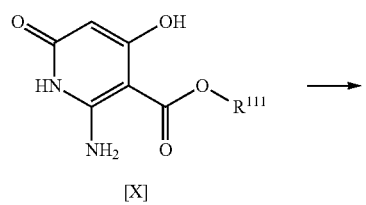

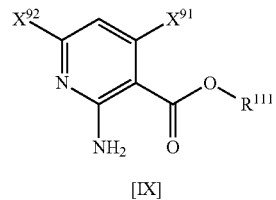

wherein $X^{91}$ and $X^{92}$ are each independently a leaving group and $R^{111}$ is a carboxy-protecting group.

Compound [IX] or a salt thereof with an acid (preferably, Compound [IX]) is obtained by converting a hydroxy group of Compound [X] or a salt thereof with an acid or base to a leaving group. The reaction is performed according to a conventional method.

For example, when both the leaving groups $X^{91}$ and $X^{92}$ are chlorine, Compound [X] or a salt thereof with an acid is chlorinated using a chlorinating reagent such as thionyl chloride, oxalylchloride, triphosgene, phosphorus pentachloride, phosphorus oxychloride and the like without solvent or in a solvent. Where necessary, it is performed in the presence of a base such as triethylamine, pyridine, 4-(dimethylamino)pyridine, N-methylmorpholine, diisopropylethylamine, tetramethylethylenediamine and the like, and N,N-dimethylformamide as necessary. As for the chlorinating reagent, phosphorus oxychloride is preferably used and, in this case, the chlorination reaction is preferably performed in the presence of diisopropylethylamine.

Examples of the solvent when the reaction is performed in a solvent include hexane, ethyl acetate, acetone, chloroform, methylene chloride, toluene, 1,4-dioxane, tetrahydrofuran, 1,2-dimethoxyethane, dimethyl sulfoxide, N,N-dimethylformamide, 2-pyrrolidone, acetonitrile, or a mixture thereof.

The chlorinating reagent is used in 2 equivalents to 30 equivalents, preferably 7 equivalents to 15 equivalents, particularly preferably 10 equivalents, relative to Compound [X].

The base is used in 1 equivalent to 3 equivalents, preferably 1.5 equivalents to 2.5 equivalents, particularly preferably 1.8 equivalents, relative to Compound [X].

The reaction temperature is 15° C. to the boiling point of the solvent, preferably 20° C. to 30° C., particularly preferably 25° C.

The reaction time is 1 hr to 72 hr, preferably 6 hr to 24 hr, particularly preferably 18 hr.

Alternatively, Compound [X] or a salt thereof with an acid or base may be reacted with p-toluenesulfonyl chloride, methanesulfonyl chloride, trifluoromethanesulfonyl chloride or anhydride thereof, or trifluoroacetyl chloride or an anhydride thereof to produce an active ester wherein both the leaving groups $X^{91}$ and $X^{92}$ are p-toluenesulfonyloxy, methanesulfonyloxy, trifluoromethanesulfonyloxy, or trifluoroacetyloxy (Compound [IX] or a salt thereof with an acid).

After completion of the reaction in this step and before performing the reaction of the next step, Compound [IX] or a salt thereof with an acid is preferably isolated to mainly remove the residue of chlorination such as chlorinating reagent and the like.

Step 3

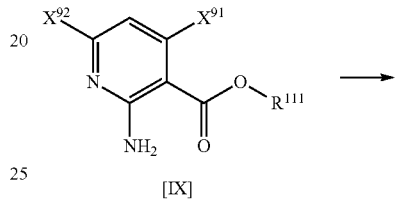

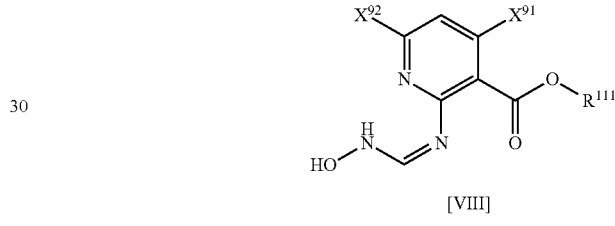

wherein $X^{91}$ and $X^{92}$ are each independently a leaving group and $R^{111}$ is a carboxy-protecting group.

Compound [IX] or a salt thereof with an acid is sequentially reacted with N,N-dimethylformamide dialkylacetal (e.g., N,N-dimethylformamide dimethyl acetal), hydroxylamine or a salt thereof (preferably, hydroxylamine hydrochloride) to give Compound [VIII] or a salt thereof with an acid (preferably, Compound [VIII]). In the present specification, the structural formula of Compound [VIII] (and below-mentioned Compound (8)) is indicated as cis form for convenience. Compound [VIII] (and below-mentioned Compound (8)) may be present as any of a cis form alone, a trans form alone and a mixture of cis form and trans form.

The reaction is performed by reacting in advance Compound [IX] or a salt thereof with an acid with N,N-dimethylformamide dialkylacetal in a solvent and adding hydroxylamine or a salt thereof.

Examples of the solvent include ethyl acetate, chloroform, toluene, 1,4-dioxane, tetrahydrofuran, 1,2-dimethoxyethane, methanol, ethanol, 2-propanol, dimethyl sulfoxide, N,N-dimethylformamide, acetonitrile, or a mixture thereof. Among the examples, 2-propanol is preferable.

N,N-dimethylformamide dialkylacetal is used in 1.0 equivalent to 10 equivalents, preferably 1.0 equivalent to 1.5 equivalents, particularly preferably 1.2 equivalents, relative to Compound [IX].

Hydroxylamine or a salt thereof is used in 1.0 equivalent to 10 equivalents, preferably 1.0 equivalent to 1.5 equivalents, particularly preferably 1.2 equivalents, relative to Compound [IX].

The reaction temperature and reaction time are 15° C. to the boiling point of the solvent for 0.5 hr to 72 hr, preferably 60° C. to 70° C. for 2 hr to 12 hr, particularly preferably 70° C. for 3 hr, when reacted with N,N-dimethylformamide dialkylacetal, and 15° C. to 30° C. for 0.5 hr to 72 hr, preferably 20° C. to 30° C. for 1 hr to 12 hr, particularly preferably 25° C. for 4 hr, after addition of hydroxylamine or a salt thereof.

After completion of the reaction in this step and before performing the reaction of the next step, Compound [VIII] or a salt thereof with an acid is preferably isolated to mainly remove impurities.

Step 4

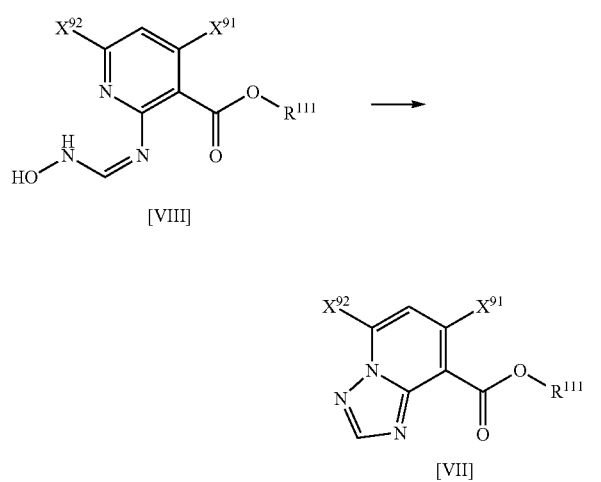

wherein $X^{91}$ and $X^{92}$ are each independently a leaving group and $R^{111}$ is a carboxy-protecting group.

Compound [VII] or a salt thereof with an acid (preferably, Compound [VII]) is obtained by a dehydration reaction of Compound [VIII] or a salt thereof with an acid.

The reaction is performed in a solvent in the presence of a dehydrating agent such as polyphosphoric acid, thionyl chloride, phosphorus oxychloride, p-toluenesulfonyl chloride, acetic anhydride, acetyl chloride, trifluoroacetic anhydride and the like. As for the dehydrating agent, trifluoroacetic anhydride is preferably used.

Examples of the solvent include hexane, ethyl acetate, acetone, chloroform, toluene, 1,4-dioxane, tetrahydrofuran, 1,2-dimethoxyethane, dimethyl sulfoxide, N,N-dimethylformamide, acetonitrile, or a mixture thereof. Among the examples, acetonitrile is preferable.

The dehydrating agent is used in 1.0 equivalent to 1.5 equivalents, preferably 1.0 equivalent to 1.2 equivalents, particularly preferably 1.1 equivalents, relative to Compound [VIII].

The reaction temperature is 15° C. to 60° C., preferably 20° C. to 50° C., particularly preferably 25° C.

The reaction time is 0.5 hr to 72 hr, preferably 4 hr to 12 hr, particularly preferably 8 hr.

After completion of the reaction in this step and before performing the reaction of the next step, Compound [VII] or a salt thereof with an acid is preferably isolated to mainly remove impurities.

Step 5

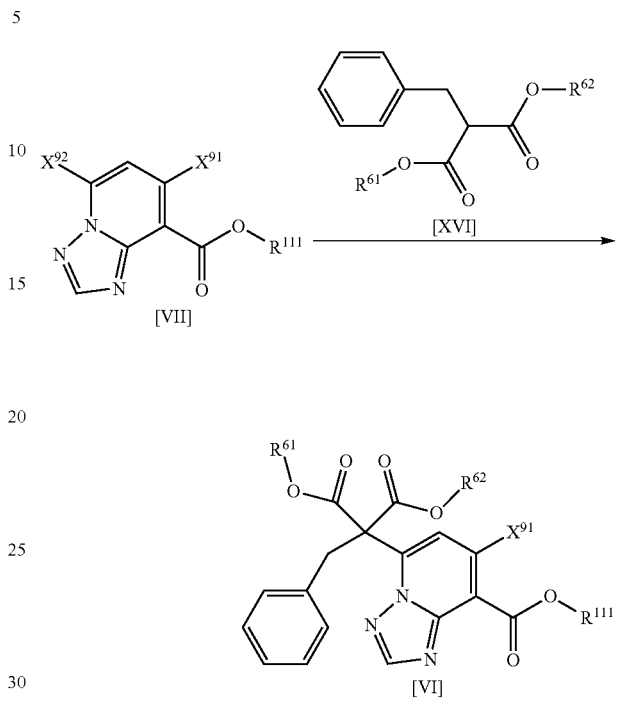

wherein $R^{61}$, $R^{62}$ and $R^{111}$ are each independently a carboxy-protecting group and $X^{91}$ and $X^{92}$ are each independently a leaving group.

Compound [VII] or a salt thereof with an acid is reacted with Benzylmalonic Acid Derivative [XVI] to give Compound [VI] or a salt thereof with an acid (preferably, Compound [VI]).

The reaction is performed in a solvent in the presence of a base such as cesium carbonate, potassium carbonate, potassium phosphate, diazabicycloundecene, N-methylmorpholine and the like. As for the base, cesium carbonate is preferably used.

Examples of the solvent include dimethyl sulfoxide, N,N-dimethylformamide, acetonitrile, toluene, tetrahydrofuran, methanol, ethanol, 1-propanol, 2-propanol, 2-methyl-1-propanol, 2-methyl-2-propanol, 1-butanol, 2-butanol, 1,4-dioxane, 1,2-dimethoxyethane, chloroform, acetone, ethyl acetate, hexane, or a mixture thereof. Among the examples, dimethyl sulfoxide is preferable.

Benzylmalonic Acid Derivative [XVI] is used in 1 equivalent to 10 equivalents, preferably 1.0 equivalent to 1.5 equivalents, particularly preferably 1.1 equivalents, relative to Compound [VII].

The base is used in 1.0 equivalent to 10 equivalents, preferably 1.0 equivalent to 1.5 equivalents, particularly preferably 1.1 equivalents, relative to Compound [VII].

The reaction temperature is 15° C. to the boiling point of the solvent, preferably 25° C. to 40° C., particularly preferably 30° C.

The reaction time is 0.5 hr to 72 hr, preferably 2 hr to 12 hr, particularly preferably 4 hr.

Step 6

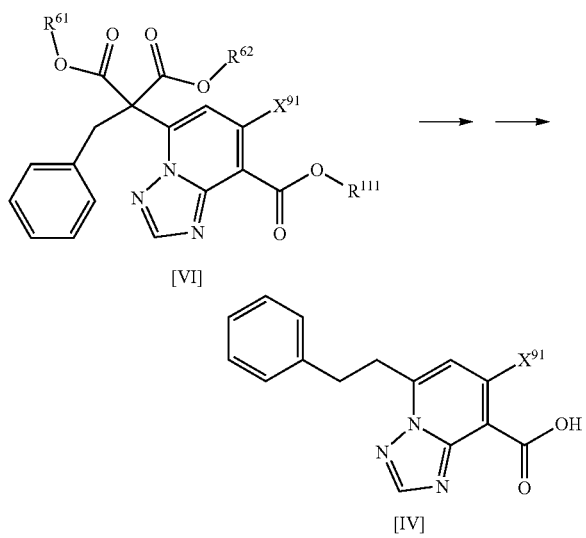

wherein $R^{61}$, $R^{62}$ and $R^{111}$ are each independently a carboxy-protecting group and $X^{91}$ is a leaving group.

Compound [VI] or a salt thereof with an acid is first hydrolyzed as shown in Operation 1, then decarboxylated as shown in Operation 2 to obtain Compound [IV] or a salt thereof with an acid or base (preferably, Compound [IV]).

Operation 1

The reaction of Operation 1 is performed in a solvent in the presence of a base such as sodium hydroxide, potassium hydroxide, lithium hydroxide, sodium carbonate, potassium carbonate, calcium hydroxide, barium hydroxide and the like. As for the base, sodium hydroxide is preferably used.

Examples of the solvent include water, methanol, ethanol, 2-propanol, tetrahydrofuran, 1,4-dioxane, 1,2-dimethoxyethane, N,N-dimethylformamide, acetonitrile, or a mixture thereof. Among the examples, a mixture of water and ethanol is preferable.

The base is used in 3 equivalents to 10 equivalents, preferably 4 equivalents to 6 equivalents, particularly preferably 5 equivalents, relative to Compound [VI].

The reaction temperature is 0° C. to 50° C., preferably 15° C. to 30° C.

The reaction time is 0.5 hr to 72 hr, preferably 1 hr to 12 hr, particularly preferably 3 hr.

Operation 2

The reaction of Operation 2 is performed in a solvent in the presence of an acid such as phosphoric acid, hydrochloric acid, sulfuric acid, acetic acid, methansulfonic acid and the like. As for the acid, hydrochloric acid is preferably used.

Examples of the solvent include water, methanol, ethanol, 2-propanol, tetrahydrofuran, 1,4-dioxane, 1,2-dimethoxyethane, N,N-dimethylformamide, acetonitrile, or a mixture thereof. Among the examples, a mixture of water and ethanol is preferable.

The acid is used in 4 equivalents to 12 equivalents, preferably 5 equivalents to 7 equivalents, particularly preferably 6 equivalents, relative to Compound [VI].

The reaction temperature is 25° C. to the boiling point of the solvent, preferably 60° C. to 80° C., particularly preferably 70° C.

The reaction time is 0.5 hr to 72 hr, preferably 2 hr to 12 hr, particularly preferably 4 hr.

The below-mentioned reactions are assumed to be performed in Operation 1

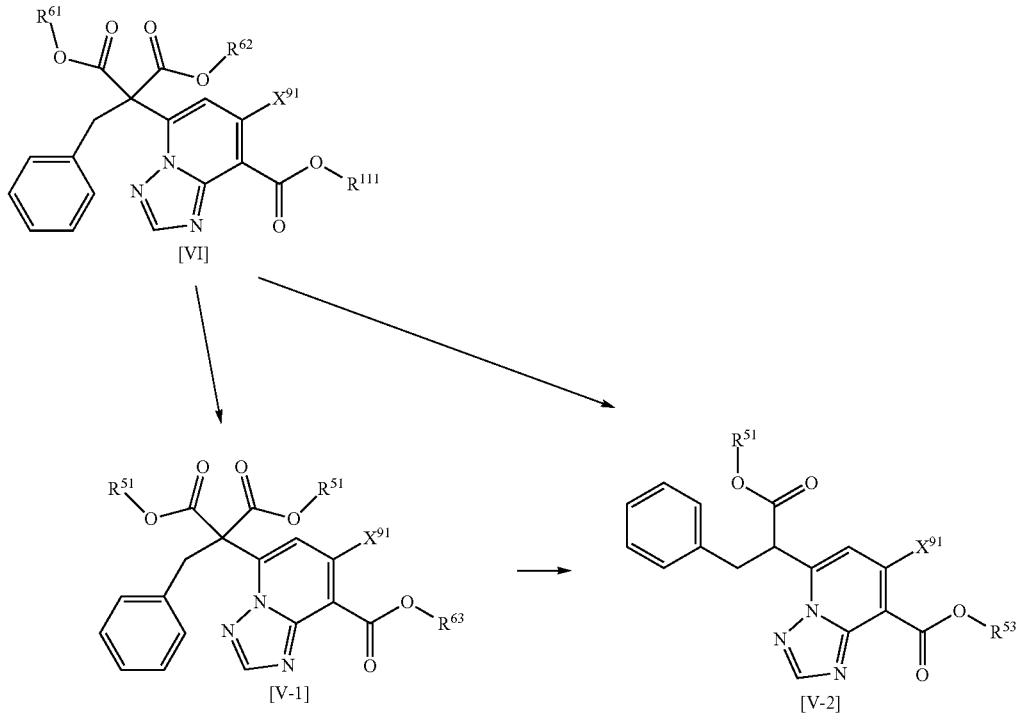

wherein $R^{51}$ and $R^{53}$ are each independently a hydrogen atom or a metal species which forms a salt with a carboxy group, $R^{51}$ in Compound [V-1] may be the same or different, $R^{61}$, $R^{62}$ and $R^{111}$ are each independently a carboxy-protecting group and $X^{91}$ is a leaving group. The resultant product obtained by Operation 1 may be any of Compound [V-1], Compound [V-2] or a mixture thereof and can be subjected to the reactions performed in the following Operation 2.

The below-mentioned reactions are assumed to be performed in Operation 2

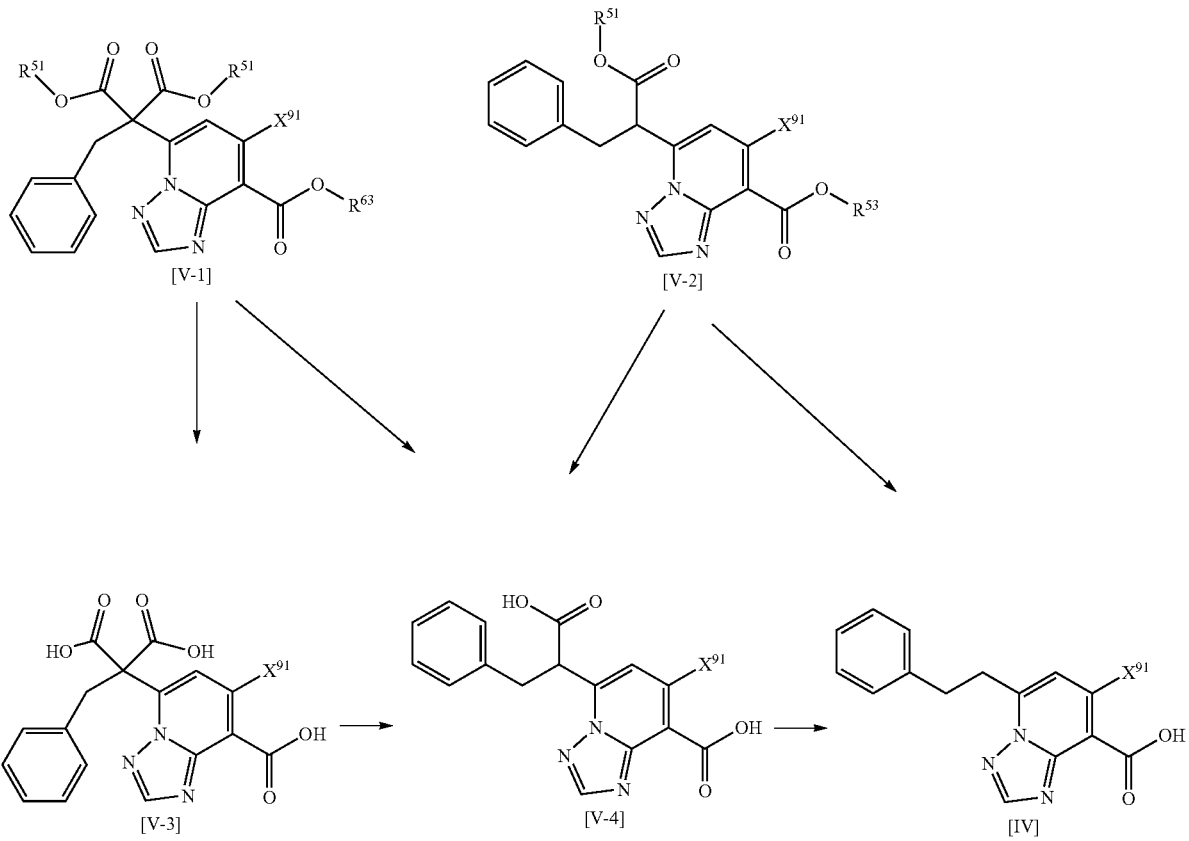

wherein $R^{51}$ and $R^{53}$ are each independently a hydrogen atom or a metal species which forms a salt with a carboxy group, $R^{51}$ in Compound [V-1] may be the same or different and $X^{91}$ is a leaving group.

After completion of the reaction in this step and before performing the reaction of the next step, Compound [IV] or a salt thereof with an acid or base is preferably isolated to mainly remove impurities.

Step 7

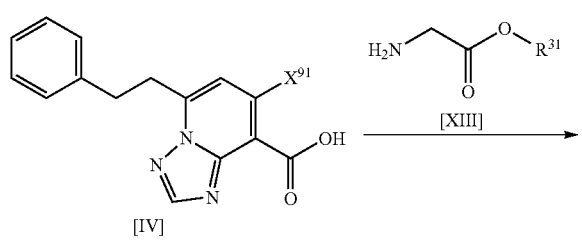

-continued

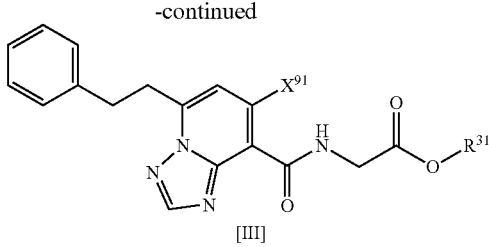

wherein $R^{31}$ is a carboxy-protecting group and $X^{91}$ is a leaving group.

Compound [IV] or a salt thereof with an acid or base is reacted with Glycine Derivative [XIII] or a salt thereof (preferably, methyl glycinate hydrochloride) to obtain Compound [III] or a salt thereof with an acid (preferably, Compound [III]).

The reaction is performed in a solvent in the presence of a condensing agent such as dicyclohexylcarbodiimide, 1,1'-carbonyldiimidazole, 1-ethyl-3-(3-dimethylaminopropyl) carbodiimide or a salt thereof, diphenylphosphoryl azide and the like and, where necessary, an additive such as N-hydroxysuccinimide, 1-hydroxybenzotriazole, dimethylaminopyridine and the like, by further adding, where necessary, a base such as potassium carbonate, sodium hydrogen carbonate, cesium carbonate, triethylamine, diisopropylethylamine, N-methylmorpholine, pyridine and the like. In particular, it is preferable to use 1-ethyl-3-(3-dimethylaminopropyl)carbodiimide monohydrochloride as the condensing agent, 1-hydroxybenzotriazole as the additive and trimethylamine as the base.

Examples of the solvent include N,N-dimethylformamide, acetonitrile, tetrahydrofuran, chloroform, ethyl acetate, methylene chloride, toluene, water, or a mixture thereof. Among the examples, acetonitrile or a mixture of acetonitrile and water is preferable.

Glycine Derivative [XIII] or a salt thereof is used in 1 equivalent to 3 equivalents, preferably 1 equivalent to 1.5 equivalents, particularly preferably 1.2 equivalents, relative to Compound [IV].

The condensing agent is used in 1 equivalent to 3 equivalents, preferably 1 equivalent to 1.5 equivalents, particularly preferably 1.2 equivalents, relative to Compound [IV]. Since the reaction is exothermic, the condensing agent is preferably added stepwise to prevent a rapid temperature rise.

The additive is used in 0.2 equivalents to 3 equivalents, preferably 0.3 equivalents to 1 equivalent, particularly preferably 0.3 equivalents, relative to Compound [IV].

The base is used in 1.0 equivalent to 3 equivalents, preferably 1.0 equivalent to 1.5 equivalents, particularly preferably 1.1 equivalents, relative to Compound [IV].

The reaction temperature is 15° C. to 50° C., preferably 20° C. to 30° C., particularly preferably 25° C.

The reaction time is 0.5 hr to 72 hr, preferably 1 hr to 12 hr, particularly preferably 2.5 hr.

Compound [III] or a salt thereof with an acid produced by the reaction of this step is preferably isolated to mainly remove impurities.

Step 8

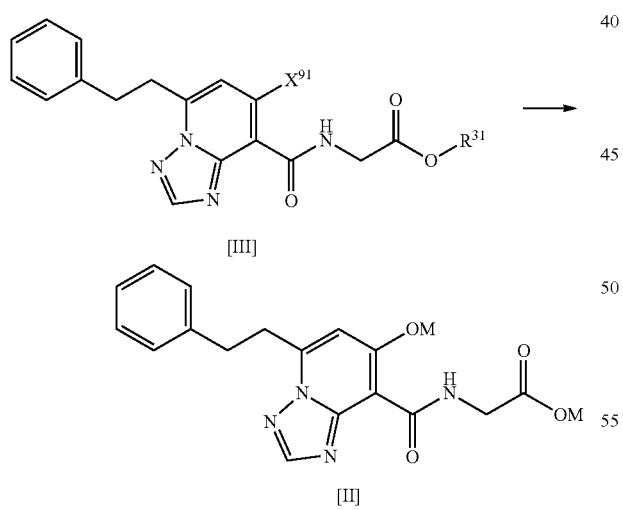

wherein $R^{31}$ is a carboxy-protecting group, $X^{91}$ is a leaving group and each M is the same and is a metal species which forms a salt with both a hydroxy group and a carboxy group.

A salt of Compound (1) with a base (Compound [III]) or a solvate thereof is obtained by reacting a base with Compound [III] or a salt thereof with an acid. For example, a sodium salt of Compound (1) (Compound (2):

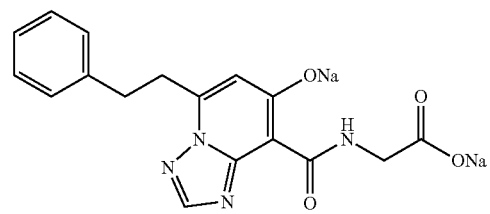

or a solvate thereof is obtained by reacting with sodium hydroxide in a solvent.

Examples of the solvent include dimethyl sulfoxide, N,N-dimethylformamide, dimethylacetamide, acetonitrile, tetrahydrofuran, 1,4-dioxane, 1,2-dimethoxyethane, toluene, methanol, ethanol, 2-methoxyethanol, 2-ethoxyethanol, 2-propanol, 1-butanol, 2-butanol, 1-pentanol, 2-pentanol, 1-hexanol, 2-hexanol, 3-hexanol, 1-heptanol, benzyl alcohol, 1,2-propanediol, water, or a mixture thereof. Among the examples, 2-ethoxyethanol or a mixture of 2-ethoxyethanol and water is preferable.

In cases where sodium hydroxide is used as the base, sodium hydroxide is used in 3 equivalents to 10 equivalents, preferably 3 equivalents to 6 equivalents, particularly preferably 5.6 equivalents, relative to Compound [III].

The reaction temperature is 60° C. to the boiling point of the solvent, preferably 80° C. to 100° C., particularly preferably 87° C.

The reaction time is 1 hr to 72 hr, preferably 3 hr to 10 hr, particularly preferably 9.5 hr.

After completion of the reaction in this step and before performing the reaction of the next step, a salt of Compound (1) with a base or a solvate thereof is preferably isolated to mainly remove impurities.

Step 9

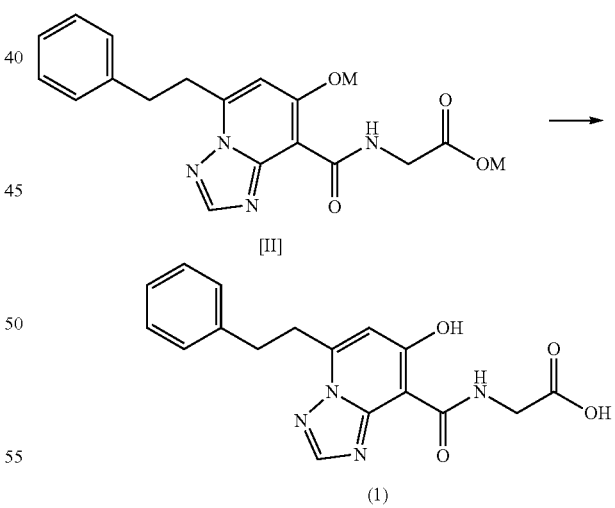

wherein each M is the same and is a metal species which forms a salt with both a hydroxy group and a carboxy group.

The salt of Compound (1) with a base (Compound [III]) or a solvate thereof is reacted with an acid such as hydrochloric acid, hydrobromic acid, phosphoric acid, sulfuric acid, acetic acid, p-toluenesulfonic acid, methanesulfonic acid, trifluoroacetic acid and the like in a solvent to obtain Compound (1). As for the acid, hydrochloric acid (concentrated hydrochloric acid) is preferably used.

Examples of the solvent include dimethyl sulfoxide, N,N-dimethylformamide, acetone, acetonitrile, tetrahydrofuran, 1,4-dioxane, 1,2-dimethoxyethane, toluene, methanol, ethanol, 2-methoxyethanol, 2-ethoxyethanol, 2-propanol, 1-butanol, 2-butanol, 1-pentanol, 2-pentanol, 1-hexanol, 2-hexanol, 3-hexanol, 1-heptanol, benzyl alcohol, 1,2-propanediol, water, or a mixture thereof. Among the examples, acetone or a mixture of acetone and water is preferable.

The acid is used in 2 equivalents to 4 equivalents, preferably 2 equivalents to 2.5 equivalents, particularly preferably 2.1 equivalents, relative to the salt of Compound (1) with a base.

The reaction temperature is 0° C. to 60° C., preferably 45° C. to 60° C., particularly preferably 50° C.

The reaction time is 0.1 hr to 72 hr, preferably 0.5 hr to 2 hr, particularly preferably 0.5 hr.

After the reaction of this step, the obtained mixture is stirred to precipitate Compound (1) as crystals.

Conversion of the crystal form of Compound (1) is performed using a mixture of alcohol (ethanol, 1-propanol, 2-propanol etc.) and water and the like as a solvent. A mixture of 2-propanol and water is preferable.

Specific characteristics of the production method include the following.

(A) Although three steps are required to obtain Compound [IV] or a salt thereof from Compound [VII], isolation and purification are not required between each step; and thus the reaction can be performed conveniently.

(B) In the step to obtain Compound [VI] from Compound [VII], the 5-position leaving group of [1,2,4]triazolo[1,5-a]pyridine is substituted with a benzylmalonic acid derivative with a high selectivity, and Compound [VI] can be produced in a highly efficient manner. Furthermore, the step does not require harsh conditions such as high temperature and the presence of a strong base.

(C) The step to obtain Compound [IV] or a salt thereof from Compound [VI] requires neither harsh reaction conditions nor strict control.

(D) In comparison with a known production method (production method described in WO 2011/007856), the production method of the present invention needs to remove neither palladium nor iron and thus there is no need to control the residue, reduces the amount of work required for preparing the starting material, and can obtain Compound [IV] or a salt thereof in a higher yield.

(E) As a result, Compound (1) or a pharmaceutically acceptable salt thereof can be produced conveniently and in a highly efficient manner.

EXAMPLES

While the present invention is explained in detail by referring to the following Examples, the present invention is not limited thereto.

Note that % indicates mol/mol % for yield, and wt % for others unless particularly indicated. In addition, room temperature indicates a temperature of 15° C. to 30° C. unless particularly indicated. The $^1$H-NMR values in the following were measured with a resolution 400 MHz.

The measurement of X-ray diffraction pattern of the samples by powder X-ray diffractometry was performed under the following conditions.

Measurement Device: X'Pert Pro (Spectris Co., Ltd.)
<Measurement Condition>
X-ray: Cu/45 kV/40 mA
  Movement: oscillating, Mode: x, Range: 4 mm
Incident Light (Incident Beam Path)
  PreFIX module: Mirror Cu W/Si (focusing MPD)
  Soller slit: Soller 0.04 rad.
  Mirror: Inc. Beam Cu W/Si (focusing MPD)
  Mask: Mask Fixed 4 mm
  Divergence slit: Slit Fixed 1/2°
  Anti-scatter slit: Slit Fixed 1/2
Diffraction Light (Diffracted Beam Path)
  PreFIX module: X'Celerator
  Soller slit: Soller 0.04 rad.
  Anti-scatter slit: none
  Detector: X'Celerator
  Mode: scanning
  effective width (2Theta): 2.122
Scan Axis: 2 θ
Gonio Angle (Other Gonio Angle)
  Omaga: 0°
Scan Mode: Continuous
  Start angle: 3°
  End angle: 25°
  Unit per step time: 10 sec
Repeated: Wobbled scan,
  Wobbled Axis: Omega
  Number of steps: 3
  Step size: 3°

Example 1

Production of 2-({[7-hydroxy-5-(2-phenylethyl)-[1,2,4]triazolo[1,5-a]pyridin-8-yl]carbonyl}amino)acetic acid (Compound (1))

Step 1

Method 1

In a reaction vessel were charged 1,2-dimethoxyethane (680 kg), dimethyl 3-oxo-1,5-pentanedioate (Compound (11))/purity 95% (193 kg, 1.05 kmol) and cyanamide (133 kg, 3.16 kmol), and the solid was dissolved by stirring. To the solution was added nickel (II) acetylacetonate (27.0 kg, 105 mol) and the mixture was stirred for 0.5 hr. Subsequently, the inside temperature of the mixture was raised to 55° C. over 0.5 hr, and the mixture was stirred at inside temperature 55° C. to 65° C. for approximately 2 hr. Then, the inside temperature of the mixture was raised to 70° C., and the mixture was stirred for approximately 8 hr while maintaining the inside temperature at 70° C. to 75° C. After completion of the reaction, the reaction mixture was cooled to an inside temperature of 25° C., and the mixture was stirred for 7.5 hr while maintaining the inside temperature at 25° C. The precipitated crystals were collected by filtration and washed with 1,2-dimethoxyethane (340 kg).

In a reaction vessel was charged methanol (464 kg), the total amount of the obtained wet crystals were charged therein, and the mixture was stirred for 3 hr at inside temperature 20° C. Thereafter, the crystals were collected by filtration and washed with methanol (150 kg). The obtained wet crystals were dried under reduced pressure to give methyl 2-amino-4-hydroxy-6-oxo-1,6-dihydropyridine-3-carboxylate (Compound (10)) (148 kg, 804 mol, yield 76.6%).

NMR and MS of the compound synthesized according to the above-mentioned method were measured.

$^1$H-NMR (DMSO-$d_6$) δ: 11.48 (brs, 1H), 10.25 (brs, 1H), 7.19 (brs, 2H), 4.92 (s, 1H), 3.81 (s, 3H).

MS: m/z=185 [M+H]$^+$

Method 2

To a mixture of dimethyl 3-oxo-1,5-pentanedioate (Compound (11)) (no conversion of purity, 99.05 kg, 568 mol), nickel chloride (3.70 kg, 28.5 mol) and sodium acetate (4.64 kg, 56.6 mol) in a reaction vessel were added acetonitrile (38.9 kg), water (4.98 kg) and acetic acid (1.74 kg, 28.9 mol). To this mixture was added cyanamide (25.20 kg, 599 mol) over 1 hr, and the vessel used was washed with acetonitrile (38.9 kg) and the washing solution was added to this mixture. The mixture was stirred for 72 hr at inside temperature 20° C. to 35° C. Disappearance of Compound (11) and production of a reaction intermediate were confirmed by high performance liquid chromatography. Then, to this reaction mixture was added methanol (15.8 kg) at room temperature, and 28% aqueous ammonia (13.9 kg, 229 mol) was added. To this mixture was added 5 mol/L aqueous sodium hydroxide solution (137.8 kg, 565 mol) at room temperature. This mixture was stirred at room temperature for 15 min. After completion of the reaction, acetonitrile (74.0 kg) and water (4.71 kg) were added to the reaction mixture, and the mixture was stirred at inside temperature 15° C. for 3 hr. Crystals were collected by filtration from the obtained suspension and washed with a mixed solution of acetonitrile (69.7 kg), methanol (35.5 kg) and water (14.9 kg) and further washed with acetonitrile (77.7 kg). The obtained wet crystals were charged in a reaction vessel and water (495.4 kg) and methanol (157.1 kg) were added thereto. To the suspension was added 28% aqueous ammonia (13.92 kg, 229 mol) at an inside temperature 23° C., and a solution of ammonium chloride (30.40 kg, 568 mol) in water (99.1 kg) was added dropwise at inside temperature 30° C. to 32° C. The obtained suspension was stirred at inside temperature 32° C. for 1 hr, and at room temperature for 4.5 hr. It was confirmed that the solution had pH between 2.5 and 5. Crystals were collected by filtration from the obtained suspension and washed with a mixed solution of methanol (29.4 kg) and water (111.4 kg), and further with methanol (78.6 kg). The obtained wet crystals were dried under reduced pressure to give methyl 2-amino-4-hydroxy-6-oxo-1,6-dihydropyridine-3-carboxylate (Compound (10)) (75.92 kg, 412 mol, yield 72.5%.

NMR and MS of the compound synthesized according to the above-mentioned method were measured.

$^1$H-NMR (DMSO-$d_6$) δ: 11.48 (brs, 1H), 10.25 (brs, 1H), 7.19 (brs, 2H), 4.92 (s, 1H), 3.81 (s, 3H).

MS: m/z=185 [M+H]$^+$

Step 2

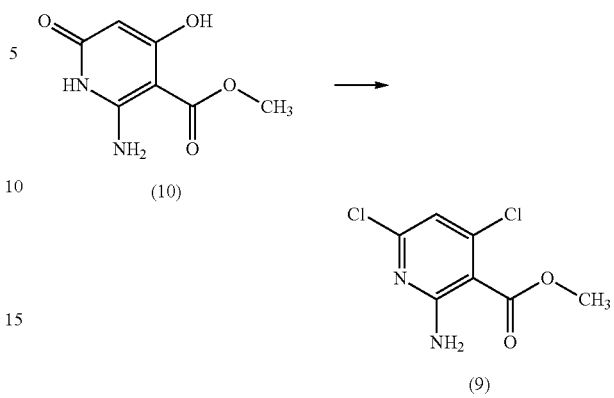

In a reaction vessel were charged phosphorus oxychloride (864 kg) and methyl 2-amino-4-hydroxy-6-oxo-1,6-dihydropyridine-3-carboxylate (Compound (10)) (105 kg, 570 mol), and the mixture was stirred at inside temperature 20° C. for 1 hr. To the mixture was added dropwise diisopropylethylamine (133 kg, 1.03 kmol) at inside temperature 11° C. to 26° C. and the mixture was stirred at inside temperature 25° C. for 18 hr.

After completion of the reaction, the reaction mixture was added dropwise to water (2.21 t) charged in another vessel at inside temperature 42° C. to 56° C. After completion of the dropwise addition, the reaction vessel was washed with acetonitrile (41 kg), and the washing solution was added to the above-mentioned another vessel and the mixture was stirred at inside temperature 45° C. for 0.5 hr. Subsequently, to the mixture was added dropwise 28% aqueous ammonia solution (849 kg) at inside temperature 8° C. to 19° C., after which the mixture was stirred at inside temperature 20° C. for 0.5 hr. The mixture was stirred at inside temperature 70° C. for 1 hr, cooled to inside temperature 30° C. and stirred at around the same temperature for 2 hr. The precipitated crystals were collected by filtration and washed with water (840 kg). The obtained wet crystals were dried under reduced pressure to give methyl 2-amino-4,6-dichloropyridine-3-carboxylate (Compound (9)) (96.3 kg, 436 mol, yield 76.5%).

NMR and MS of the compound synthesized according to the above-mentioned method were measured.

$^1$H-NMR (DMSO-$d_6$) δ: 7.16 (brs, 2H), 6.83 (s, 1H), 3.84 (s, 3H).

MS: m/z=221 [M+H]$^+$

Step 3

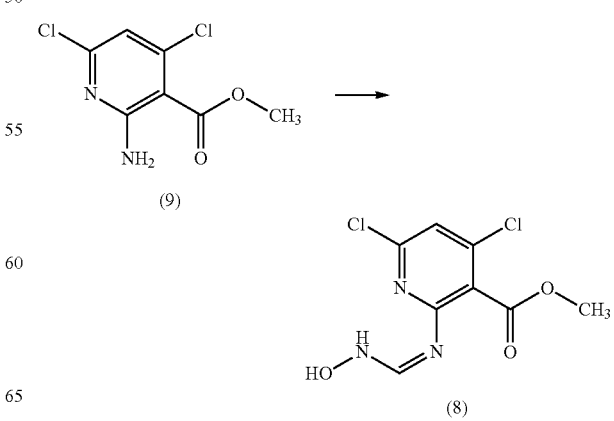

In a reaction vessel were charged 2-propanol (1.18 t) and methyl 2-amino-4,6-dichloropyridine-3-carboxylate (Compound (9)) (189 kg, 855 mol). To the mixture was added dropwise dimethylformamide dimethylacetal/purity 98.7% (122 kg, 1.01 kmol) at inside temperature 63° C. to 70° C. and the mixture was stirred at 70° C. for 3 hr.

Successively, to this reaction mixture was added hydroxylamine hydrochloride (71.1 kg, 1.02 kmol) at 25° C. and the mixture was stirred at 25° C. for 4 hr. After completion of the reaction, to the reaction mixture was added dropwise water (1.13 t) at inside temperature 21° C. to 30° C. and the mixture was stirred at the same temperature for 1 hr. The precipitated crystals were collected by filtration and washed twice with a mixed solution of 2-propanol (169 kg) and water (162 kg). The obtained wet crystals were dried under reduced pressure to give methyl 4,6-dichloro-2-[(N-hydroxyformimidoyl)-amino]pyridine-3-carboxylate (Compound (8)) (175 kg, 663 mol, yield 77.5%).

NMR and MS of the compound synthesized according to the above-mentioned method were measured.

$^1$H-NMR (DMSO-$d_6$) δ: 10.80 (s, 1H), 10.10 (d, 1H, J=9.2 Hz), 7.84 (d, 1H, J=9.2 Hz), 7.35 (s, 1H), 3.93 (s, 3H).

MS: m/z=264 [M+H]$^+$

Step 4

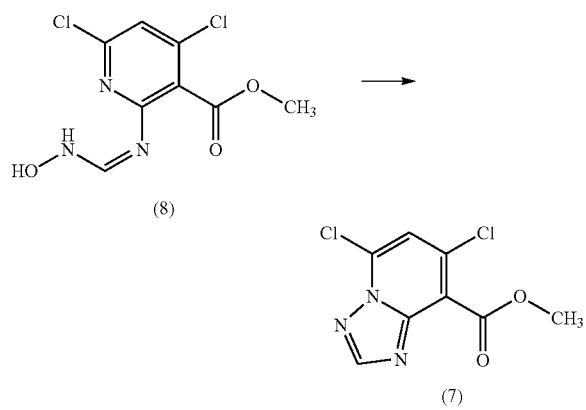

In a reaction vessel were charged acetonitrile (824 kg) and trifluoroacetic anhydride (154 kg). To this solution was added portionwise methyl 4,6-dichloro-2-[(N-hydroxyformimidoyl)-amino]pyridine-3-carboxylate (Compound (8)) (175 kg, 663 mol) at inside temperature 6° C. to 16° C., and the reaction mixture was stirred at inside temperature 20° C. to 26° C. for 8 hr.

After completion of the reaction, a suspension of activated carbon (53 kg) in toluene (382 kg) was added to the said reaction mixture at inside temperature 2° C. to 8° C., and the mixture was stirred at inside temperature 1° C. to 3° C. for 0.5 hr. To the mixture was added dropwise N-methylmorpholine (155 kg) at inside temperature 1° C. to 9° C., and the mixture was stirred at inside temperature 2° C. to 7° C. for 1 hr. Subsequently, the mixture was filtered and the filtered activated carbon was washed with toluene (76 kg). The filtrate and the washing solution were combined, washed with water (702 kg), partitioned, and the aqueous layer was extracted with toluene (608 kg). The organic layer and the toluene layer were combined, washed with water (702 kg), partitioned, and the organic layer was concentrated under reduced pressure at outer temperature 55° C. to 60° C. Successively, 2-propanol (828 kg) was added to the residue and the mixture was concentrated under reduced pressure at outer temperature 55° C. to 60° C. 2-Propanol (828 kg) was added again to the residue and the mixture was concentrated under reduced pressure at outer temperature 55° C. to 60° C. To the obtained residue was added 2-propanol (996 kg), the liquid volume was adjusted to 1579 L and the mixture was recrystallized successively. The crystallized solution was stirred at 2° C. to 10° C. for 2 hr, collected by filtration, and the crystals were washed with 2-propanol (276 kg) cooled to 0° C. to 10° C. The obtained wet crystals were dried under reduced pressure to give methyl (5,7-dichloro-[1,2,4]triazolo[1,5-a]pyridin-8-yl)carboxylate (Compound (7)) (135 kg, 549 mol, yield 82.8%).

NMR and MS of the compound synthesized according to the above-mentioned method were measured.

$^1$H-NMR (DMSO-$d_6$) δ: 8.71 (s, 1H), 7.91 (s, 1H), 3.99 (s, 3H).

MS: m/z=246 [M+H]$^+$

The powder X-ray diffraction pattern of the crystal of Compound (7) synthesized by a method similar to the above-mentioned method is shown in FIG. 1. The vertical axis shows diffraction intensity (cps: counts per second) and the horizontal axis shows diffraction angle 2 θ(°).

According to FIG. 1, each peak is as follows. Diffraction angle: 2 θ(°)=9.7, 11.3, 12.5, 14.2, 15.9, 16.9, 17.2, 19.6, 20.7, 21.3, 22.7, 23.4, 24.4.

(Crystal of Hydrochloride of Compound (7))

To a suspension of Compound (7) (5.00 g, 20.3 mmol) in ethyl acetate (25 mL) and toluene (25 mL) was added 4 mol/L hydrogen chloride ethyl acetate solution (5.6 mL, 22.4 mmol) at room temperature. The suspension was stirred at room temperature. Crystals were collected by filtration and washed with ethyl acetate. The obtained wet crystals were dried under reduced pressure to give methyl (5,7-dichloro-[1,2,4]triazolo[1,5-a]pyridin-8-yl)carboxylate hydrochloride (hydrochloride of Compound (7)) (5.32 g, 18.8 mmol, yield 92.6%).

Figure 2:
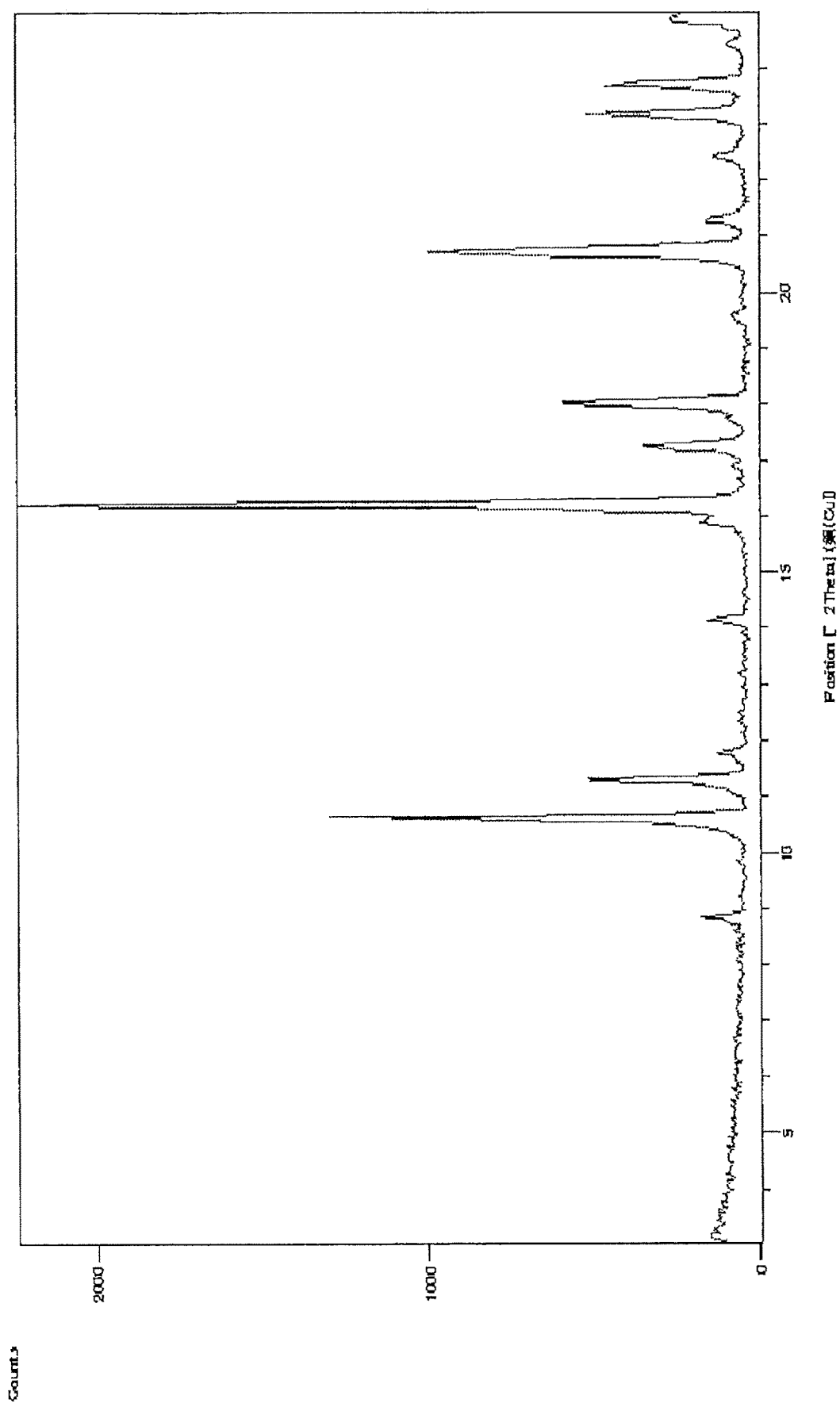
FIG. 2 shows a powder X-ray diffraction pattern of a crystal of hydrochloride of Compound (7) synthesized in Step 4 of Example 1.

The powder X-ray diffraction pattern of the crystal of hydrochloride of Compound (7) synthesized by a method similar to the above-mentioned method is shown in FIG. 2. The vertical axis shows diffraction intensity (cps: counts per second) and the horizontal axis shows diffraction angle 2 θ(°).

According to FIG. 2, each peak is as follows. Diffraction angle: 2 θ(°)=8.9, 10.6, 11.3, 11.8, 14.1, 16.2, 17.3, 18.0, 19.6, 20.7, 21.3, 22.4, 23.2, 23.7.

Step 5

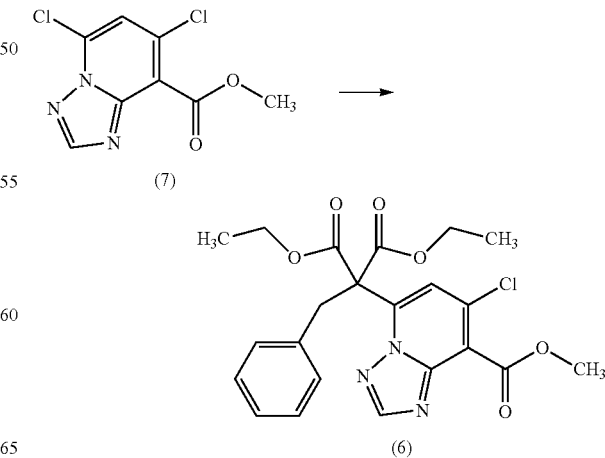

To a solution of methyl (5,7-dichloro-[1,2,4]triazolo[1,5-a]pyridin-8-yl)carboxylate (Compound (7)) (50.0 g, 203 mmol) in dimethyl sulfoxide (250 mL) were added diethyl benzylmalonate (Compound (16)) (55.8 g, 223 mmol) and cesium carbonate (72.7 g, 223 mmol) at room temperature, and the mixture was stirred at 30° C. for 4 hr. After completion of the reaction, toluene (400 mL) was added to the reaction mixture at room temperature, and water (400 mL) was added to the solution under ice-cooling. The aqueous layer was separated, the obtained organic layer was filtered to remove insoluble materials. The vessel was washed with toluene (100 mL) and the combined organic layer was washed twice with 5% brine (150 mL). The solvent was evaporated under reduced pressure from the obtained organic layer. Ethanol (500 mL) was added thereto and the solvent was evaporated under reduced pressure. Ethanol was added to the residue and the liquid volume was adjusted to 250 mL to give an ethanol solution of methyl 5-[1,1-di(ethoxycarbonyl)-2-phenylethyl]-7-chloro-[1,2,4]triazolo[1,5-a]pyridine-8-carboxylate (Compound (6)) (corresponding to 203 mmol).

NMR and MS of the compound synthesized according to the above-mentioned method and precipitated from the ethanol solution were measured.

$^1$H-NMR (DMSO-d$_6$) δ: 8.73 (s, 1H), 7.42 (s, 1H), 7.17-7.08 (m, 3H), 6.68-6.65 (m, 2H), 4.26-4.13 (m, 4H), 3.99 (s, 3H), 3.87 (s, 2H), 1.09 (t, 6H, 6.8 Hz).

MS: m/z=460 [M+H]$^+$

Step 6

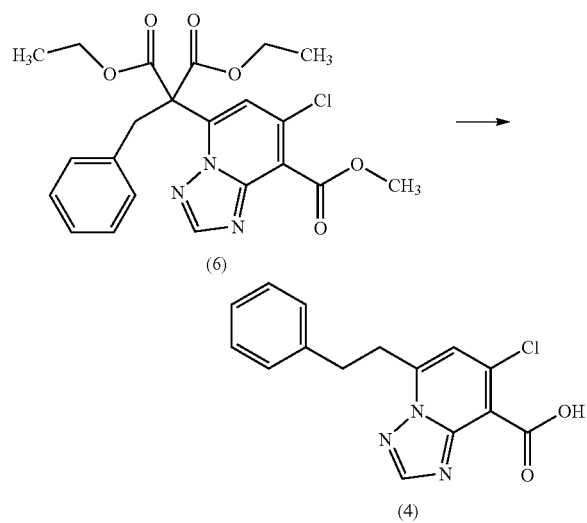

To a solution of methyl 5-[1,1-di(ethoxycarbonyl)-2-phenylethyl]-7-chloro-[1,2,4]triazolo[1,5-a]pyridine-8-carboxylate (Compound (6)) (203 mmol) in ethanol was added dropwise 4 mol/L aqueous sodium hydroxide solution (250 mL, 1.00 mol) at room temperature over 1.5 hr, and the mixture was stirred at the same temperature for 1.5 hr. After completion of the reaction, water (75 mL) was added to the mixture. The obtained solution was added dropwise to a mixed solution of 6 mol/L hydrochloric acid (200 mL, 1.20 mol) and ethanol (125 mL) at room temperature. The obtained suspension was stirred at room temperature for 0.5 hr, further at 60° C. for 4 hr and at 70° C. for 2 hr. After completion of the reaction, the mixture was cooled to room temperature and stirred for 1.5 hr. The precipitated crystals were collected by filtration and washed with a mixed solution of ethanol (150 mL) and water (150 mL). The obtained wet crystals were dried under reduced pressure to give 7-chloro-5-(2-phenylethyl)-[1,2,4]triazolo[1,5-a]pyridine-8-carboxylic acid (Compound (4)) (57.6 g, 191 mmol, yield 94.1%).

NMR and MS of the compound synthesized according to the above-mentioned method were measured.

$^1$H-NMR (DMSO-d$_6$) δ: 14.16 (brs, 1H), 8.64 (s, 1H), 7.33-7.19 (m, 6H), 3.47-3.43 (m, 2H), 3.13 (dd, 2H, J=8.4 Hz, 6.0 Hz).

MS: m/z=302 [M+H]$^+$

Figure 3:
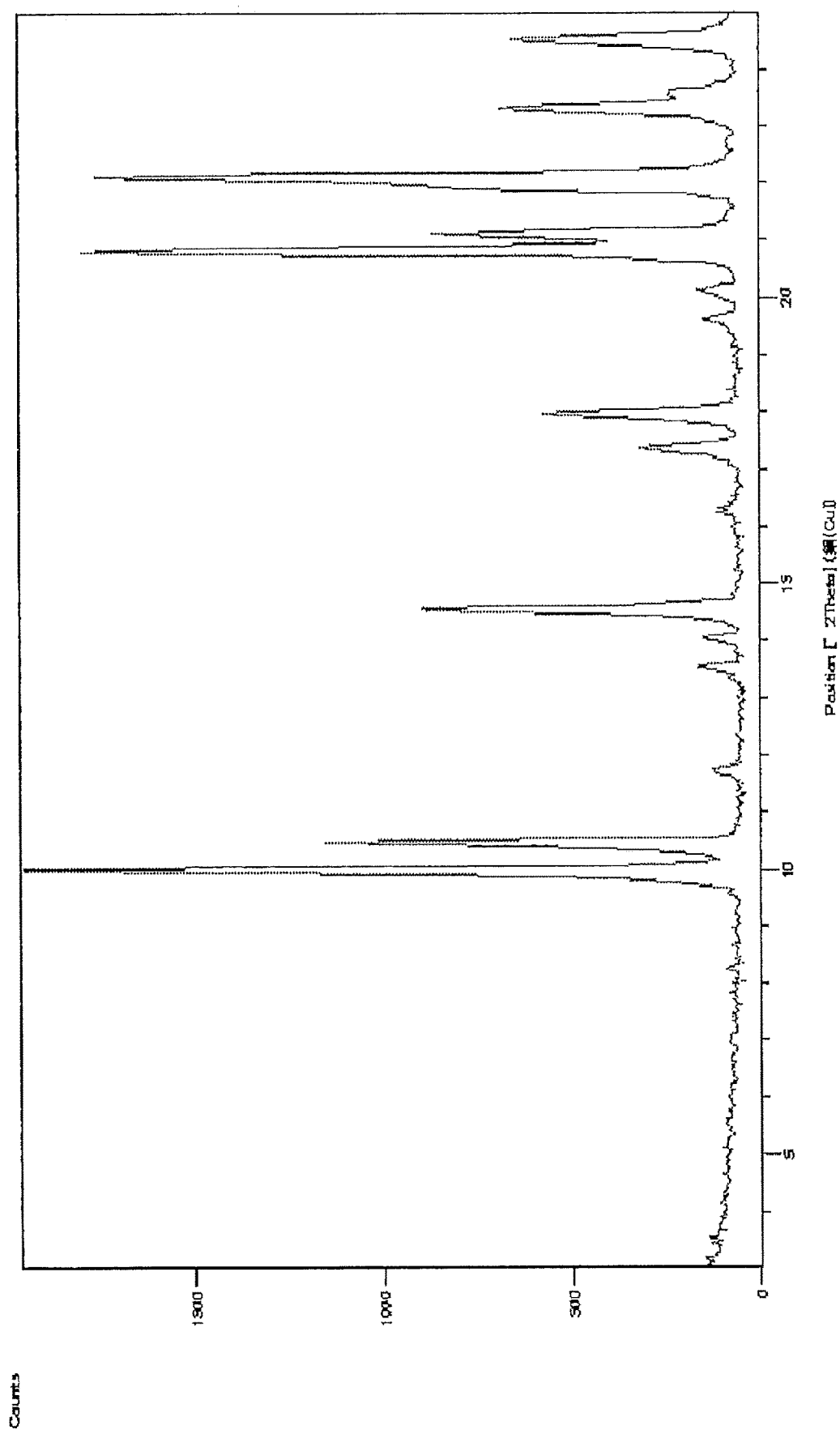
FIG. 3 shows a powder X-ray diffraction pattern of crystal I of Compound (4) synthesized in Step 6 of Example 1.

The powder X-ray diffraction pattern of the crystal of Compound (4) synthesized by a method similar to the above-mentioned method is shown in FIG. 3. The vertical axis shows diffraction intensity (cps: counts per second) and the horizontal axis shows diffraction angle 2 θ(°).

According to FIG. 3, each peak is as follows. Diffraction angle: 2 θ(°)=10.0, 10.5, 11.7, 13.5, 14.0, 14.6, 16.3, 17.4, 18.0, 19.6, 20.1, 20.8, 21.1, 22.1, 23.3, 24.5.

(Crystal II of Compound (4))

To a solution of methyl 5-[1,1-di(ethoxycarbonyl)-2-phenylethyl]-7-chloro-[1,2,4]triazolo[1,5-a]pyridine-8-carboxylate (Compound (6)) (corresponding to 40.6 mmol) in ethanol was added dropwise 4 mol/L aqueous sodium hydroxide solution (50 mL, 200 mmol) at room temperature, and the mixture was stirred at the same temperature for 2 hr. After completion of the reaction, ethanol (25 mL) was added to the mixture. To the mixture was added 6 mol/L hydrochloric acid (26 mL, 156 mmol) and the mixture was stirred at inside temperature 77° C. for 6.5 hr. After completion of the reaction, the mixture was cooled to room temperature. To the obtained suspension was added dropwise 6 mol/L hydrochloric acid (6.77 mL, 40.6 mmol) at inside temperature 43° C., and the mixture was stirred at the same temperature for 3 hr. This suspension was stirred at room temperature for 2 hr and crystals were collected by filtration. The obtained wet crystals were dried under reduced pressure to give 7-chloro-5-(2-phenylethyl)-[1,2,4]triazolo[1,5-a]pyridine-8-carboxylic acid (Compound (4)) (10.067 g, 33.4 mmol, yield 82.3%).

NMR and MS of the compound synthesized according to the above-mentioned method were measured.

$^1$H-NMR (DMSO-d$_6$) δ: 14.16 (brs, 1H), 8.64 (s, 1H), 7.33-7.19 (m, 6H), 3.47-3.43 (m, 2H), 3.13 (dd, 2H, J=8.4 Hz, 6.0 Hz).

Figure 4:
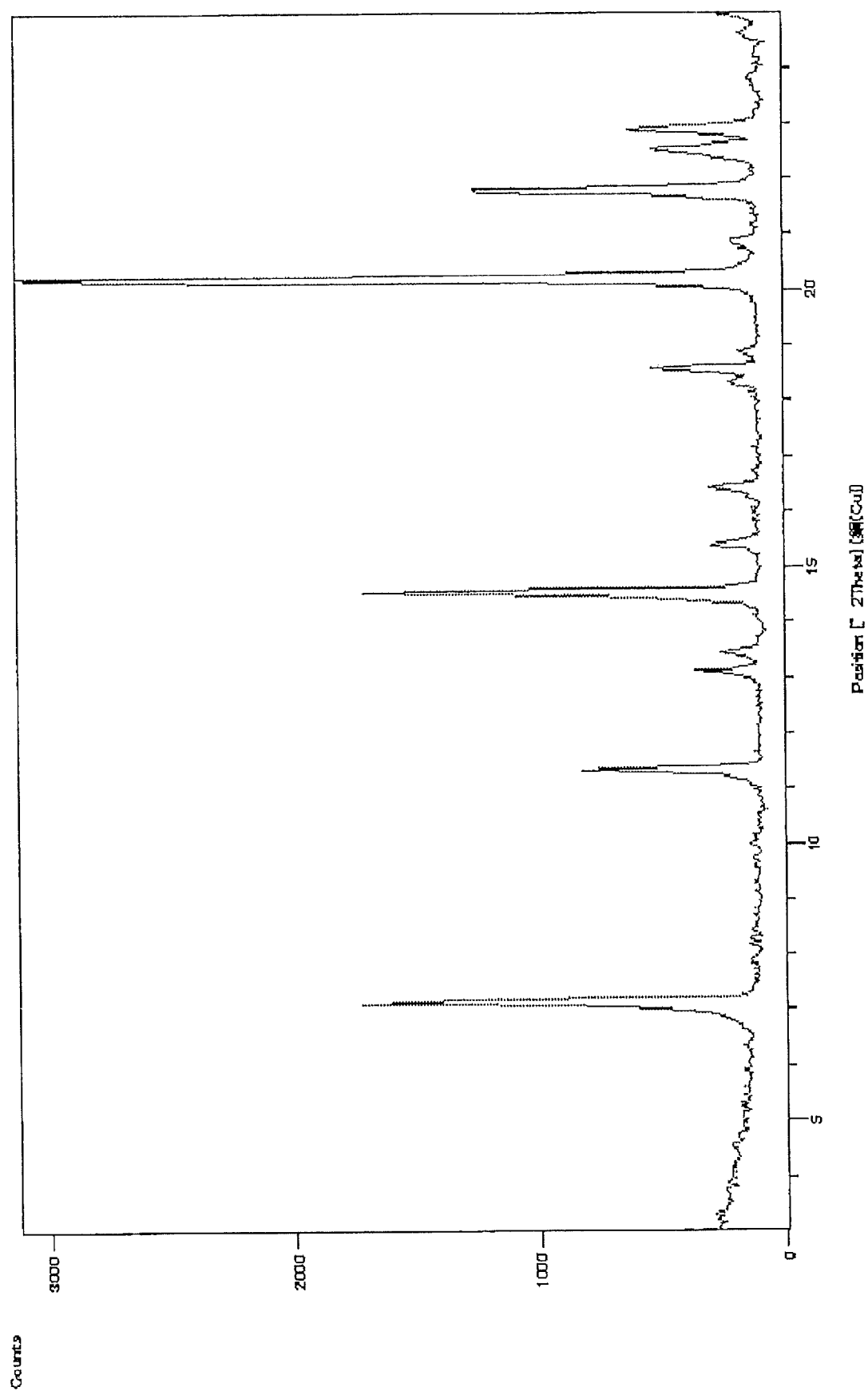
FIG. 4 shows a powder X-ray diffraction pattern of crystal II of Compound (4) synthesized in Step 6 of Example 1.

The powder X-ray diffraction pattern of the crystal of Compound (4) synthesized by a method similar to the above-mentioned method is shown in FIG. 4. The vertical axis shows diffraction intensity (cps: counts per second) and the horizontal axis shows diffraction angle 2 θ(°).

According to FIG. 4, each peak is as follows. Diffraction angle: 2 θ(°)=7.1, 11.3, 13.1, 13.5, 14.5, 15.4, 16.4, 18.6, 20.2, 20.9, 21.8, 22.5, 22.9, 24.6.

(Crystal of Sodium Salt of Compound (4))

To a suspension of 7-chloro-5-(2-phenylethyl)-[1,2,4]triazolo[1,5-a]pyridine-8-carboxylic acid (Compound (4)) (3.7 g, 12.3 mmol) in ethanol (15 mL)/water (12 mL) was added 4 mol/L aqueous sodium hydroxide solution (3.0 mL, 12 mmol) at room temperature. The suspension was heated to inside temperature 61° C. and a mixed solution of ethanol (1.5 mL) and water (1.5 mL) was added thereto. Furthermore, 4 mol/L aqueous sodium hydroxide solution was added and dissolution of solid was confirmed. The solution was cooled to room temperature, and crystals were collected by filtration and washed with ethanol. The obtained wet crystals were dried under reduced pressure to give sodium 7-chloro-5-(2-phenylethyl)-[1,2,4]triazolo[1,5-a]pyridine-8-carboxylate (sodium salt of Compound (4)) (1.67 g, 5.16 mmol, yield 42.0%).

Figure 5:
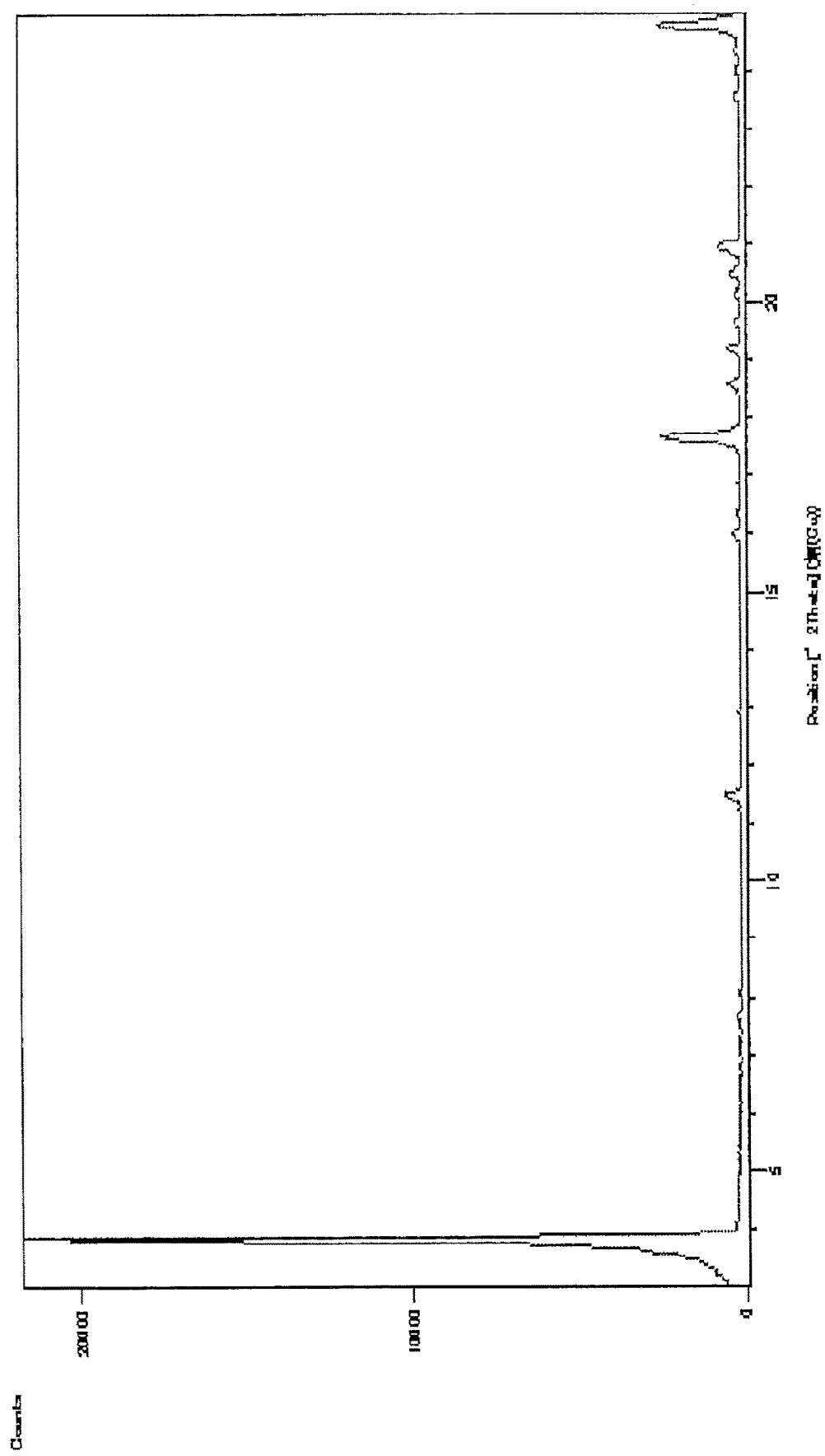
FIG. 5 shows a powder X-ray diffraction pattern of a crystal of sodium salt of Compound (4) synthesized in Step 6 of Example 1.

The powder X-ray diffraction pattern of the crystal of sodium salt of Compound (4)) synthesized by a method similar to the above-mentioned method is shown in FIG. 5. The vertical axis shows diffraction intensity (cps: counts per second) and the horizontal axis shows diffraction angle 2 θ(°).

According to FIG. 5, each peak is as follows. Diffraction angle: 2 θ(°)=3.8, 7.7, 11.5, 12.9, 16.0, 17.7, 18.6, 19.2, 19.7, 20.1, 20.5, 21.0, 21.5, 23.6, 24.0, 24.4, 24.8.

(Crystal of Hydrochloride of Compound (4))

To a suspension of 7-chloro-5-(2-phenylethyl)-[1,2,4]triazolo[1,5-a]pyridine-8-carboxylic acid (Compound (4)) (5.00 g, 16.6 mmol) in ethyl acetate (50 mL) was added 4 mol/L hydrogen chloride ethyl acetate solution (20.71 mL, 104 mmol) at room temperature. The obtained suspension was stirred at room temperature. Crystals were collected by filtration and washed with ethyl acetate (20 mL). The obtained wet crystals were dried under reduced pressure to give 7-chloro-5-(2-phenylethyl)-[1,2,4]triazolo[1,5-a]pyridine-8-carboxylic acid hydrochloride (hydrochloride of Compound (4)) (5.54 g, 16.4 mmol, yield 98.8%).

Figure 6:
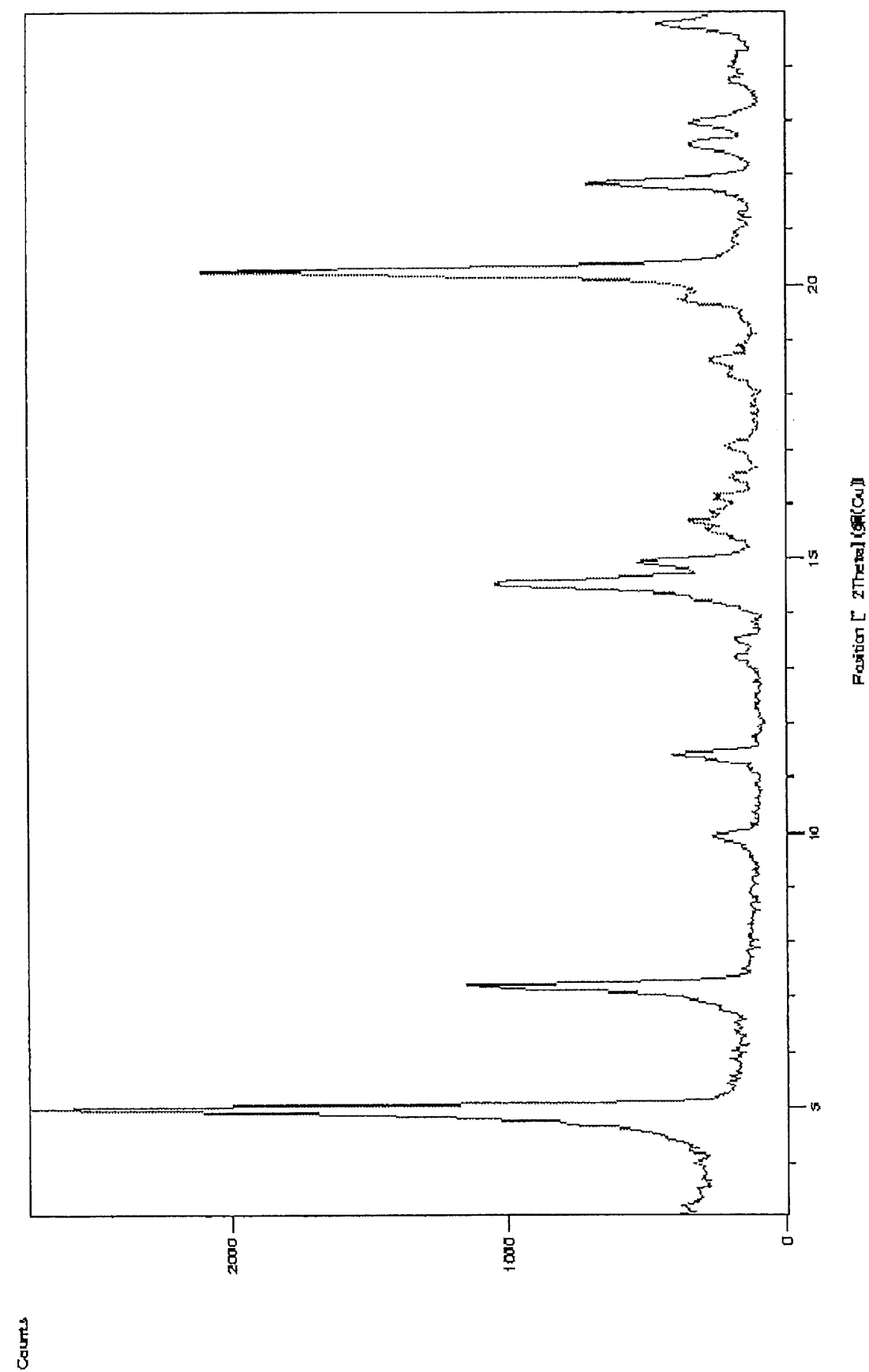
FIG. 6 shows a powder X-ray diffraction pattern of a crystal of hydrochloride of Compound (4) synthesized in Step 6 of Example 1.

The powder X-ray diffraction pattern of the crystal of hydrochloride of Compound (4) synthesized by a method similar to the above-mentioned method is shown in FIG. 6. The vertical axis shows diffraction intensity (cps: counts per second) and the horizontal axis shows diffraction angle 2 θ(°).

According to FIG. 6, each peak is as follows. Diffraction angle: 2 θ(°)=5.0, 7.2, 9.9, 11.4, 13.3, 14.6, 15.0, 15.7, 16.1, 16.5, 17.1, 18.7, 19.7, 20.3, 21.8, 22.6, 23.0, 24.8.

Step 7

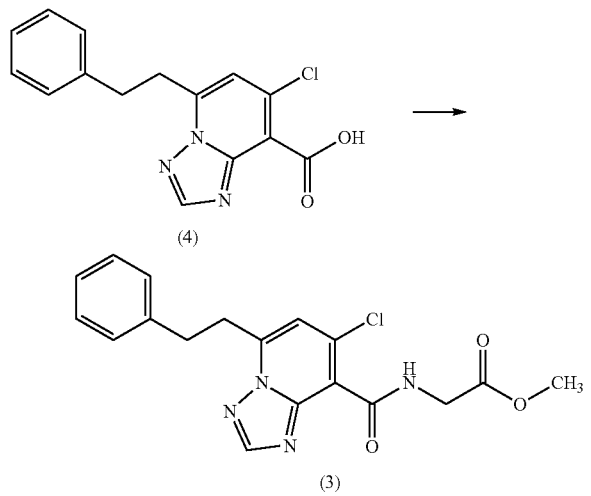

Method 1

To a suspension of 7-chloro-5-(2-phenylethyl)-[1,2,4]triazolo[1,5-a]pyridine-8-carboxylic acid (Compound (4)) (27.5 kg, 91.1 mol) in acetonitrile (140 L) were added 1-hydroxybenzotriazole monohydrate (16.7 kg, 109 mol), trimethylamine (11.0 kg, 109 mol), methyl glycinate hydrochloride (hydrochloride of Compound (13)) (13.7 kg, 109 mol) at room temperature. To this mixture was added 1-ethyl-3-(3-dimethylaminopropyl)carbodiimide monohydrochloride (20.9 kg, 109 mol) in four portions over 0.5 hr at room temperature for the purpose of controlling heat generation. The mixture was stirred at room temperature for 2 hr. After completion of the reaction, 5% aqueous sodium bicarbonate (280 L) was added dropwise at room temperature, and the mixture was stirred at the same temperature for 1 hr. The precipitated crystals were collected by filtration and washed with a mixed solution of ethanol (77.5 L) and water (77.5 L). The obtained wet crystals were charged in a mixed solution of ethanol (70 L) and water (70 L), and the suspension was stirred at room temperature for 23 hr. The precipitated crystals were collected by filtration and washed with a mixed solution of ethanol (77.5 L) and water (77.5 L). The obtained wet crystals were dried under reduced pressure to give methyl 2-({[7-chloro-5-(2-phenylethyl)-[1,2,4]triazolo[1,5-a]pyridin-8-yl]carbonyl}amino)acetate (Compound (3)) (29.3 kg, 78.6 mol, yield 86.3%).

Method 2

To a suspension of 7-chloro-5-(2-phenylethyl)-[1,2,4]triazolo[1,5-a]pyridine-8-carboxylic acid (Compound (4)) (200 g, 663 mmol) in acetonitrile (600 mL) and water (200 mL) were added 1-hydroxybenzotriazole monohydrate (30.5 g, 199 mmol), triethylamine (73.8 g, 729 mmol), methyl glycinate hydrochloride (hydrochloride of Compound (13)) (99.9 g, 796 mmol) at room temperature. To this mixture was added 1-ethyl-3-(3-dimethylaminopropyl)carbodiimide hydrochloride (153 g, 798 mmol) in four portions over 1 hr at room temperature for the purpose of controlling heat generation. The mixture was stirred at room temperature for 1 hr. After completion of the reaction, water (1.0 L) was added to the reaction mixture at room temperature. The obtained suspension was stirred at the same temperature for 1 hr. The precipitated crystals were collected by filtration and washed with a mixed solution of methanol (0.6 L) and water (0.6 L). The obtained wet crystals were dried under reduced pressure to give methyl 2-({[7-chloro-5-(2-phenylethyl)-[1,2,4]triazolo[1,5-a]pyridin-8-yl]carbonyl}amino)acetate (Compound (3)) (234 g, 628 mmol, yield 94.7%).

NMR and MS of the compound synthesized according to the above-mentioned method were measured.

$^1$H-NMR (DMSO-$d_6$) δ: 9.26 (t, 1H, J=6.0 Hz), 8.64 (s, 1H), 7.33-7.20 (m, 6H), 4.12 (d, 2H, J=6.0 Hz), 3.69 (s, 3H), 3.46 (dd, 2H, 10.0 Hz, 6.0 Hz), 3.13 (dd, 2H, J=10.0 Hz, 6.0 Hz).

MS: m/z=373 [M+H]$^+$

Step 8

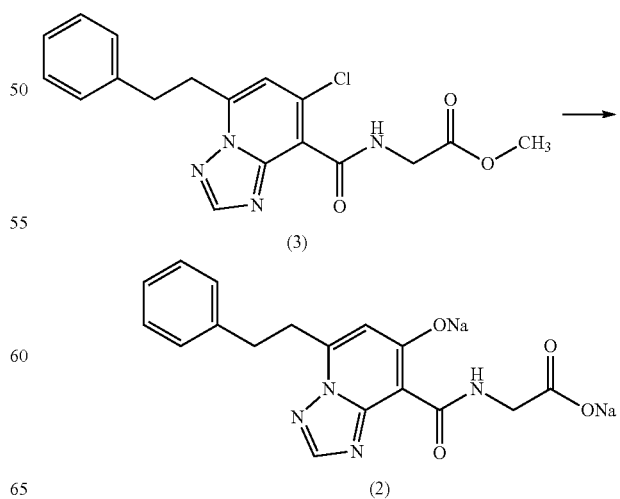

To a suspension of methyl 2-({[7-chloro-5-(2-phenyl-ethyl)-[1,2,4]triazolo[1,5-a]pyridin-8-yl]carbonyl}amino)acetate (Compound (3)) (29.3 kg, 78.6 mol) in 2-ethoxyethanol (150 L) was added 5 mol/L aqueous sodium hydroxide solution (88 L, 440 mol), and the mixture was stirred at 87° C. for 9.5 hr. After completion of the reaction, a mixed solution of ethanol (146.5 L) and water (14.5 L) was added dropwise to the reaction mixture at 70° C. The mixture was cooled to room temperature and stirred at the same temperature for 9 hr. The precipitated crystals were collected by filtration and washed with a mixed solution of ethanol (78.3 L) and water (11.7 L). The obtained wet crystals were dried under reduced pressure to give disodium 2-({[7-hydroxy-5-(2-phenylethyl)-[1,2,4]triazolo[1,5-a]pyridin-8-yl]carbonyl}amino)acetate (Compound (2) as a salt of Compound (1)) (32.9 kg, 85.6 mol, yield 109%).

NMR and MS of the compound synthesized according to the above-mentioned method were measured.

$^1$H-NMR (DMSO-$d_6$) δ: 11.28 (t, 1H, J=4.4 Hz), 7.87 (s, 1H), 7.30-7.16 (m, 5H), 6.02 (s, 1H), 3.60 (d, 2H, J=4.4 Hz), 3.11-3.00 (m, 4H).

MS: m/z=339 [M+H−2Na]$^-$

The content of the residual solvent in the obtained compound was measured by GC.
Residual ethanol: 0.0%
Residual 2-ethoxyethanol: 9.5%

In addition, the analysis conditions of the above-mentioned measurement performed by GC were as follows.
Detection method: FID (flame ionization detector)
Column: Fused-silica Capillary Column DB-WAX (J&W Scientific) (30 m×0.53 mmI.D., film thickness 1 μm)
Detector temperature: approximately 250° C.
Sample injector: approximately 200° C.
Column temperature: maintained at 50° C. for 8 min, the temperature was raised to 120° C. at a ratio of 14° C./min and maintained at the same temperature for 10 min. Thereafter, the temperature was raised to 200° C. at a ratio of 40° C./min and maintained at the same temperature for 5 min.
Carrier gas: helium
Carrier gas flow: adjusted such that retention time of ethanol obtained from standard solution 1 μL was approximately 4.5 min
Split ratio: approximately 1/10
Injection volume: 1 μL
Analysis time: 15 min.
Step 9

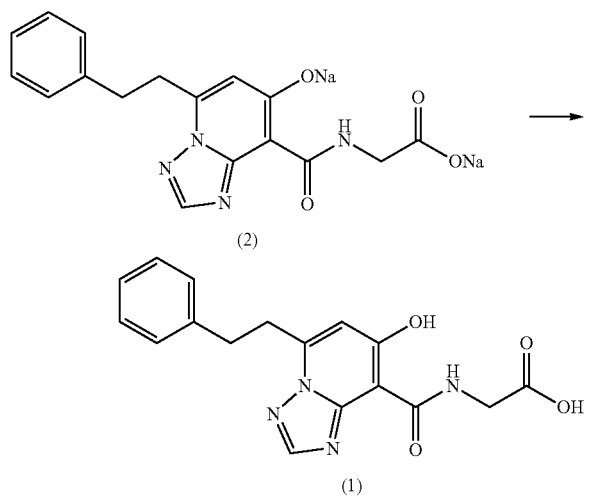

To a solution of disodium 2-({[7-hydroxy-5-(2-phenylethyl)-[1,2,4]triazolo[1,5-a]pyridin-8-yl]carbonyl}amino)acetate (Compound (2) as a salt of Compound (1)) (32.9 kg, 85.6 mol) in water (120 L) was added 5 mol/L aqueous sodium hydroxide solution (1.6 L, 8.00 mol), and the mixture was stirred at 33° C. for 1 hr. To the solution was added activated carbon (3.30 kg) suspended in water (16.3 L) and the mixture was stirred at 34° C. for 1.5 hr. The suspension was filtered and the obtained filtrate was added dropwise to a mixed solution of concentrated hydrochloric acid (18.7 kg, 180 mol), water (17 L) and acetone (230 L) at 48° C. To the mixture was added a seed crystal (16.5 g) of 2-({[7-hydroxy-5-(2-phenylethyl)-[1,2,4]triazolo[1,5-a]pyridin-8-yl]carbonyl}amino)acetic acid, and the mixture was stirred at 48° C. for 2 hr. To the obtained suspension was added dropwise water (66 L) at 48° C., and the mixture was stirred at the same temperature for 1 hr. The suspension was cooled to room temperature and stirred for 1 hr. The precipitated crystals were collected by filtration and washed with a mixed solution of acetone (99 L) and water (99 L). The obtained wet crystals were dried under reduced pressure to give 2-({[7-hydroxy-5-(2-phenylethyl)-[1,2,4]triazolo[1,5-a]pyridin-8-yl]carbonyl}amino)acetic acid (Compound (1)) (20.9 kg, 61.4 mol, yield 71.7%).

NMR and MS of the compound synthesized according to the above-mentioned method were measured.

$^1$H-NMR (DMSO-$d_6$) δ: 14.24 (s, 1H), 12.98 (s, 1H), 9.84 (t, 1H, J=5.2 Hz), 8.59 (s, 1H), 7.32-7.19 (m, 5H), 6.81 (s, 1H), 4.21 (d, 2H, J=5.2 Hz), 3.41 (dd, 2H, J=8.8 Hz, 6.4 Hz), 3.12 (dd, 2H, J=8.8 Hz, 6.4 Hz).

MS: m/z=341 [M+H]$^+$

Crystal form Conversion Step

A mixed solution of 2-({[7-hydroxy-5-(2-phenylethyl)-[1,2,4]triazolo[1,5-a]pyridin-8-yl]carbonyl}amino)acetic acid (Compound (1)) (20.8 kg, 61.1 mol) obtained in the said step in 2-propanol (330 L) and water (83 L) was stirred at 77° C. and dissolution of the crystal was confirmed. The solution was cooled to 65° C. and a seed crystal (20.8 g) of 2-({[7-hydroxy-5-(2-phenylethyl)-[1,2,4]triazolo[1,5-a]pyridin-8-yl]carbonyl}amino)acetic acid (Compound (1)) was added at the same temperature. The solution was stirred at 60° C. for 2 hr, cooled to room temperature and stirred for 21 hr. The precipitated crystals were collected by filtration and washed with a mixed solution of 2-propanol (42 L) and water (42 L). The obtained wet crystals were dried under reduced pressure to give 2-{[7-hydroxy-5-(2-phenylethyl)-[1,2,4]triazolo[1,5-a]pyridin-8-yl]carbonyl}amino)acetic acid (Compound (1)) (19.3 kg, 56.7 mol, yield 92.8%).

NMR and MS of the compound synthesized according to the above-mentioned method were measured.

$^1$H-NMR (DMSO-$d_6$) δ: 14.24 (s, 1H), 12.98 (s, 1H), 9.84 (t, 1H, J=5.2 Hz), 8.59 (s, 1H), 7.32-7.19 (m, 5H), 6.81 (s, 1H), 4.21 (d, 2H, J=5.2 Hz), 3.41 (dd, 2H, J=8.8 Hz, 6.4 Hz), 3.12 (dd, 2H, J=8.8 Hz, 6.4 Hz).

MS: m/z=341 [M+H]$^+$

INDUSTRIAL APPLICABILITY

The present invention can provide a method for producing Compound (1) or a pharmaceutically acceptable salt thereof in a good yield.

In addition, compounds [V-1] and [VI] of the present invention are useful as synthetic intermediates for producing Compound (1) or a pharmaceutically acceptable salt thereof.

Furthermore, the production method of the present invention is useful as a large-scale industrial synthetic method

The invention claimed is:
1. A method for producing Compound (1):

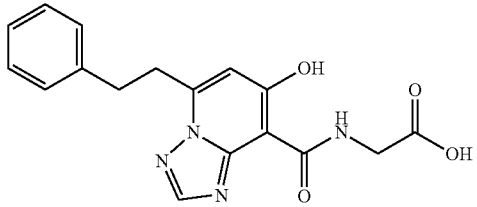

(1)

or a pharmaceutically acceptable salt thereof, the method comprising:
a step of hydrolyzing and then decarboxylating Compound [VI]:

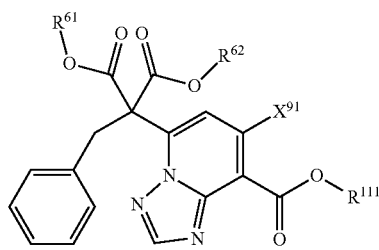

[VI]

or a salt thereof, wherein:
R$^{61}$, R$^{62}$ and R$^{111}$ are each independently selected from C$_{1-6}$ alkyl and benzyl; and
X$^{91}$ is selected from halogen, p-toluenesulfonyloxy, methanesulfonyloxy, trifluoromethanesulfonyloxy, and trifluoroacetyloxy; to give Compound [IV]:

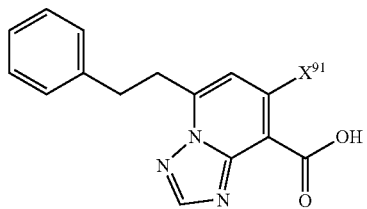

[IV]

or a salt thereof, wherein X$^{91}$ is as defined above,
a step of reacting Compound [IV] or a salt thereof with a glycine derivative to give Compound [III]:

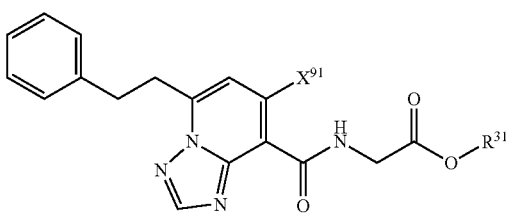

[III]

or a salt thereof, wherein:
R$^{31}$ is selected from C$_{1-6}$ alkyl and benzyl; and
X$^{91}$ is as defined above;
a step of reacting Compound [III] or a salt thereof with a base to give a salt of Compound (1), and a step of reacting the said salt of Compound (1) with an acid to give Compound (1).

2. The production method according to claim 1 further comprising:
a step of reacting Compound [VII]:

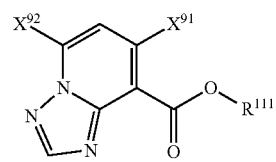

[VII]

or a salt thereof, wherein:
X$^{92}$ is selected from halogen, p-toluenesulfonyloxy, methanesulfonyloxy, trifluoromethanesulfonyloxy, and trifluoroacetyloxy; and
X$^{91}$ and R$^{111}$ are as defined above;
with a benzylmalonic acid derivative to give Compound [VI] or a salt thereof.

3. The production method according to claim 2 further comprising:
a step of reacting Compound [XI]:

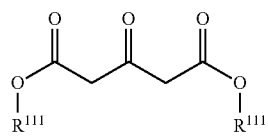

[XI]

wherein R$^{111}$ is as defined above and may be the same or different, with cyanamide or a salt thereof to give Compound [X]:

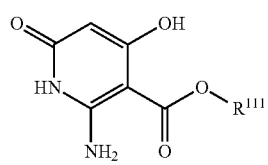

[X]

or a salt thereof, wherein R$^{111}$ is as defined above,
a step of converting a hydroxy group of Compound [X] or a salt thereof to a leaving group to give Compound [IX]:

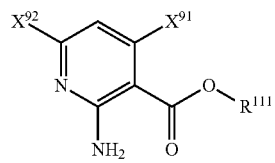

[IX]

or a salt thereof, wherein X$^{91}$, X$^{92}$ and R$^{111}$ are as defined above, a step of sequentially reacting Compound [IX] or a salt thereof with N,N-dimethylformamide dialkylacetal, hydroxylamine or a salt thereof to give Compound [VIII]:

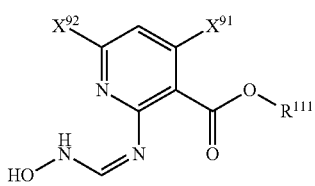

(VIII)

or a salt thereof, wherein $X^{91}$, $X^{92}$ and $R^{111}$ are as defined above, and a step of subjecting Compound [VIII] or a salt thereof to a dehydration reaction to give Compound [VII] or a salt thereof.

4. The production method according to claim 1 wherein Compound [VI] or a salt thereof is Compound (6):

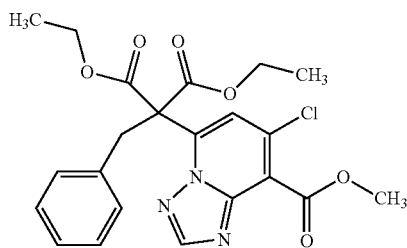

(6)

or a salt thereof, Compound [IV] or a salt thereof is Compound (4):

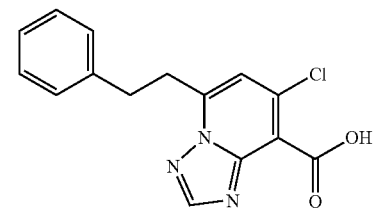

(4)

or a salt thereof, Compound [III] or a salt thereof is Compound (3):

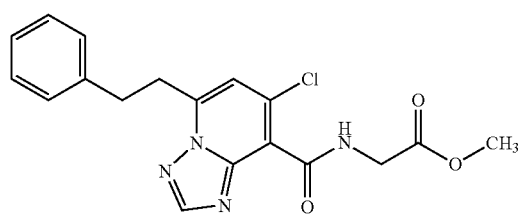

(3)

or a salt thereof, and the said salt of Compound (1) is Compound (2):

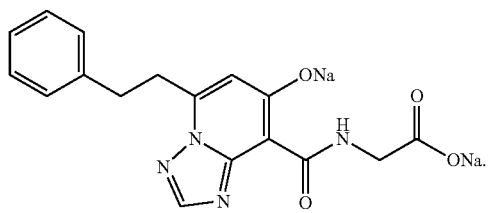

(2)

5. The production method according to claim 4 further comprising:

a step of reacting Compound (7):

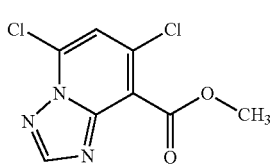

(7)

or a salt thereof with a benzylmalonic acid derivative to give Compound (6) or a salt thereof.

6. The production method according to claim 5 further comprising:

a step of reacting Compound (11):

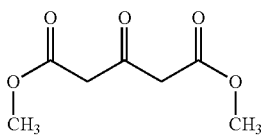

(11)

with cyanamide or a salt thereof to give Compound (10):

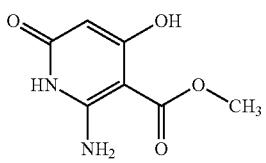

(10)

or a salt thereof, a step of chlorinating a hydroxy group of Compound (10) or a salt thereof to give Compound (9):

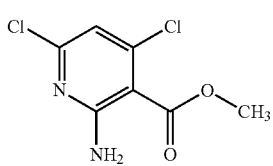

(9)

or a salt thereof, a step of reacting Compound (9) or a salt thereof with hydroxylamine or a salt thereof to give Compound (8):

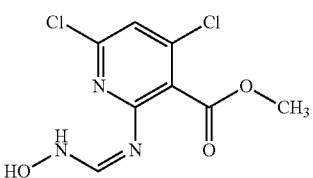 (8)

or a salt thereof, and
a step of subjecting Compound (8) or a salt thereof to a dehydration reaction to give Compound (7) or a salt thereof.

7. A method for producing Compound [VI]:

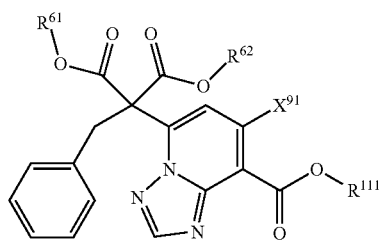 [VI]

or a salt thereof, wherein:
$R^{61}$, $R^{62}$, and $R^{111}$ are each independently selected from $C_{1-6}$ alkyl and benzyl; and
$X^{91}$ is selected from halogen, p-toluenesulfonyloxy, methanesulfonyloxy, trifluoromethanesulfonyloxy, and trifluoroacetyloxy;
the method comprising:
a step of reacting Compound [VII]:

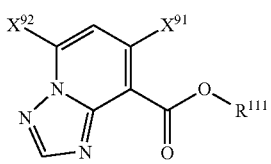 [VII]

or a salt thereof, wherein:
$X^{92}$ is selected from halogen, p-toluenesulfonyloxy, methanesulfonyloxy, trifluoromethanesulfonyloxy, and trifluoroacetyloxy; and
$X^{91}$ and $R^{111}$ are as defined above;
with a benzylmalonic acid derivative to give Compound [VI] or a salt thereof.

8. A method for producing Compound [IV]:

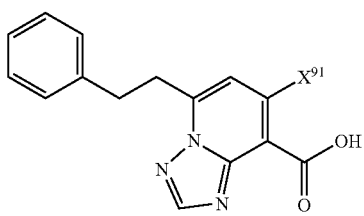 [IV]

or a salt thereof, wherein $X^{91}$ is selected from halogen, p-toluenesulfonyloxy, methanesulfonyloxy, trifluoromethanesulfonyloxy, and trifluoroacetyloxy, the method comprising:
a step of reacting Compound [VII]:

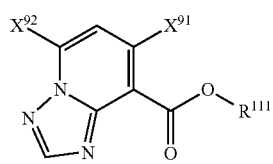 [VII]

or a salt thereof, wherein:
$X^{92}$ is selected from halogen, p-toluenesulfonyloxy, methanesulfonyloxy, trifluoromethanesulfonyloxy, and trifluoroacetyloxy;
$R^{111}$ is selected from $C_{1-6}$ alkyl and benzyl; and
$X^{91}$ is as defined above;
with a benzylmalonic acid derivative to give Compound [VI]:

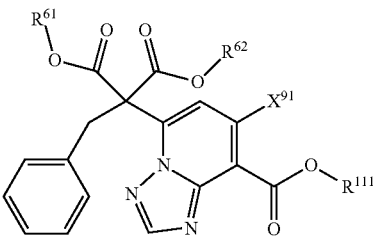 [VI]

or a salt thereof; wherein:
$R^{61}$ and $R^{62}$ are each independently selected from $C_{1-6}$ alkyl and benzyl; and
$X^{91}$ and $R^{111}$ are as defined above; and
a step of hydrolyzing and then decarboxylating Compound [VI] or a salt thereof to give Compound [IV] or a salt thereof.

9. Compound [VI]:

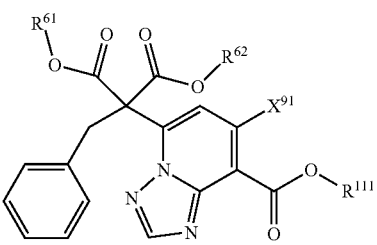 [VI]

or a salt thereof, wherein:
$R^{61}$, $R^{62}$ and $R^{111}$ are each independently selected from $C_{1-6}$ alkyl and benzyl; and
$X^{91}$ is selected from halogen, p-toluenesulfonyloxy, methanesulfonyloxy, trifluoromethanesulfonyloxy, and trifluoroacetyloxy.

* * * * *